(12) United States Patent
Krumholz

(10) Patent No.: US 11,471,048 B2
(45) Date of Patent: Oct. 18, 2022

(54) TELE-MICROSCOPIC MAGNIFYING ATTACHMENT FOR BINOCULAR INDIRECT OPHTHALMOSCOPES

(71) Applicant: The Research Foundation for SUNY, Albany, NY (US)

(72) Inventor: David M. Krumholz, Little Neck, NY (US)

(73) Assignee: The Research Foundation for SUNY, Albany, NY (US)

(*) Notice: Subject to any disclaimer, the term of this patent is extended or adjusted under 35 U.S.C. 154(b) by 390 days.

(21) Appl. No.: 16/274,186

(22) Filed: Feb. 12, 2019

(65) Prior Publication Data

US 2019/0246900 A1 Aug. 15, 2019

Related U.S. Application Data

(60) Provisional application No. 62/630,795, filed on Feb. 14, 2018.

(51) Int. Cl.
| | | |
|---|---|---|
| *A61B 3/13* | (2006.01) | |
| *A61B 3/12* | (2006.01) | |
| *A61B 3/00* | (2006.01) | |
| *A61B 3/14* | (2006.01) | |

(52) U.S. Cl.
CPC ............... *A61B 3/132* (2013.01); *A61B 3/12* (2013.01); *A61B 3/0008* (2013.01); *A61B 3/14* (2013.01)

(58) Field of Classification Search
CPC .................................. A61B 3/132; A61B 3/12
USPC .......................... 351/205–206, 246
See application file for complete search history.

(56) References Cited

U.S. PATENT DOCUMENTS

| | | | | |
|---|---|---|---|---|
| 4,397,310 A | * | 8/1983 | Pomerantzeff | A61F 9/008 219/121.6 |
| 4,682,866 A | * | 7/1987 | Volk | A61B 3/132 351/205 |
| 4,807,987 A | * | 2/1989 | Bastable | A61B 3/132 351/205 |
| 5,430,506 A | * | 7/1995 | Volk | A61B 3/125 351/205 |
| 7,347,552 B2 | * | 3/2008 | Reis | A61B 3/12 351/206 |

(Continued)

*Primary Examiner* — James R Greece
(74) *Attorney, Agent, or Firm* — Lance D. Reich; Austin Winter

(57) ABSTRACT

This present invention comprises a Galilean tele-microscope lens assembly configured to attach to the front of a binocular indirect ophthalmoscope (BIO) either permanently or by means of a clip or other suitable detachable mechanism, and to enhance an image of a patient's ocular fundus produced by a condensing lens hand-held by the examiner, at their arm's length, in front of the patient's eye. The lens assembly of the present invention magnifies the examiner's view of the hand-held condensing lens itself, and thus magnifies the fundus image produced by the hand-held condensing lens, enabling improved appreciation of finer details in an examination. In addition to improving BIO examinations in general, the present invention is especially advantageous for patients who have disabilities, are wheelchair bound, are children, or are patients of "mission" based ophthalmoscopy services provided in developing, "emerging economy" countries where other examination equipment may not be available.

20 Claims, 17 Drawing Sheets

(56) References Cited

U.S. PATENT DOCUMENTS

2012/0184846 A1* 7/2012 Izatt ................ A61B 3/132
                                                600/425
2016/0278635 A1* 9/2016 Fukuma ............ A61B 3/132

* cited by examiner

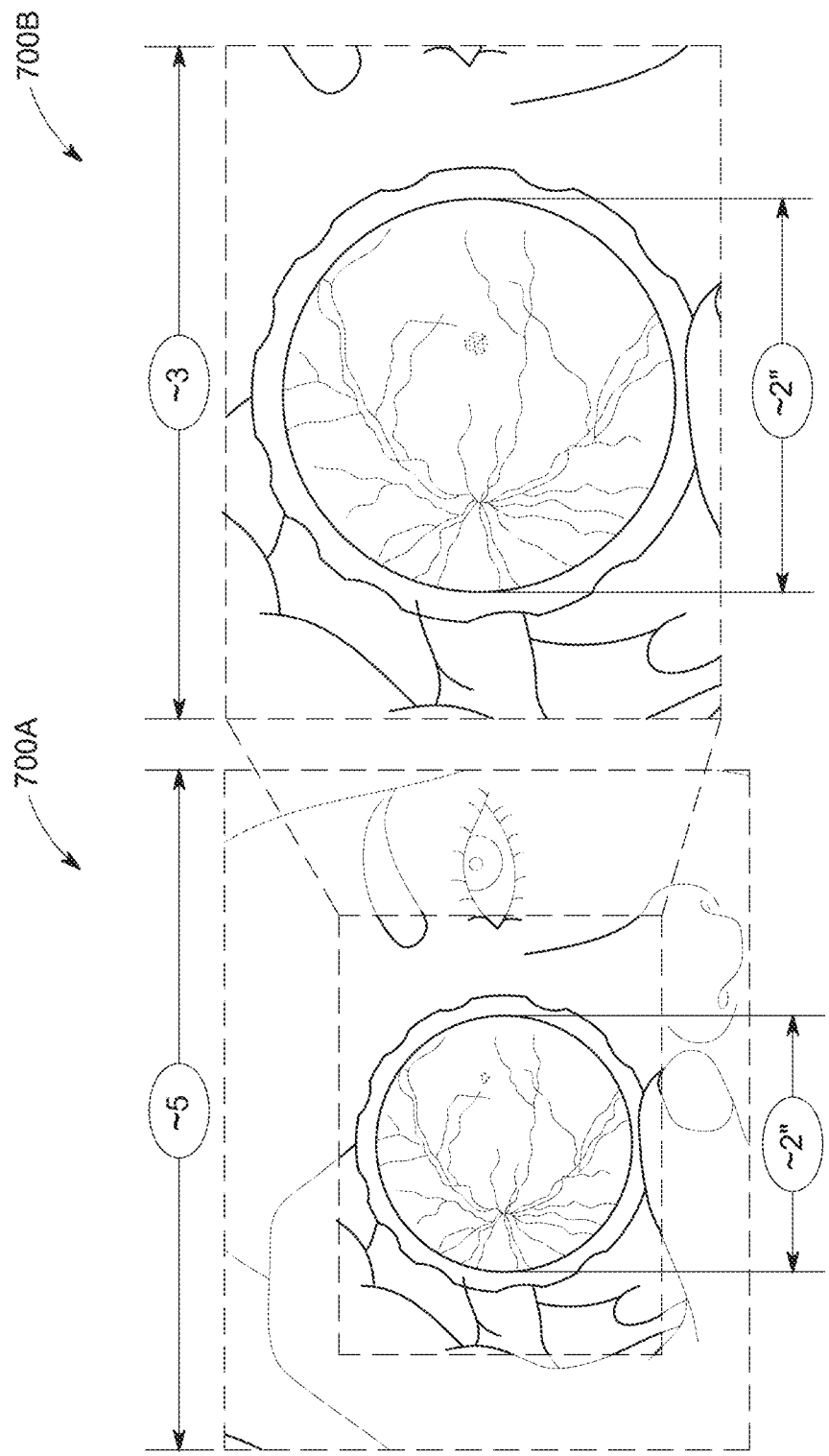

TELE-MICROSCOPIC MAGNIFYING ATTACHMENT FOR BINOCULAR INDIRECT OPHTHALMOSCOPES

BACKGROUND

1. Field of the Invention

The present invention generally relates to a novel lens assembly and system configured to provide an improved binocular indirect ophthalmoscope (hereinafter as "BIO") and an improved method of performing binocular indirect ophthalmoscopy, enabling ophthalmologists and optometrists to more clearly see aberrations and pathologies present within the ocular fundus, including the vitreous chamber, the retina, the optic nerve, the retinal vessels, the macula, the fovea, and the choroid of a patient.

2. Description of Related Art

The following description includes information that may be useful in understanding the present invention. It is not an admission that any of the information provided herein is prior art or relevant to the presently claimed invention, or that any publication specifically or implicitly referenced is prior art. All publications herein are incorporated by reference to the same extent as if each individual publication or patent application was specifically and individually indicated to be incorporated by reference.

Ophthalmoscopy, also called fundoscopy, is the procedure used to examine the interior of the eye. By properly illuminating and viewing through a subject's pupil, it is possible to see the interior of the patient's eye, which consists of the vitreous chamber (in the posterior segment of the eye), the retina, the optic nerve, the macula, the fovea, the choroid, and the retinal blood vessels (collectively referred to as the fundus). The fundus is commonly examined by using a BIO, a device worn on the examiner's head, which has a light source to illuminate the inside of the patient's eye, and reflectors to allow the examiner to see the image produced by a separate condensing lens hand-held by the examiner just in front of the patient's eye along the line of sight.

Condensing lenses are biconvex lenses, approximately 2 inches (50 mm) in diameter, with the surface that faces the examiner typically being more steeply curved than the other surface that faces the patient's eye. The condensing lens is hand-held by the examiner in front of the eye to be examined, along a line of sight from the BIO through the condensing lens, the patient's pupil, and the area of fundus under study. Optically, the condensing lens produces a real, inverted aerial image of the fundus (i.e., within the condensing lens field of view) that is formed in air close to the condensing lens, between the condensing lens and the examiner. This real, inverted aerial image of the fundus (condensing lens field of view) is what is seen by the examiner, and is located an arm's length (on the order of half a meter) from the front of the examiner's BIO headset.

Thus, the examiner is looking at an image that is approximately 50 mm in diameter, an arm's length (~50 cm) away (the viewing distance). At this viewing distance, the image of the fundus (condensing lens field of view) takes up less than half of the examiner's field of view through the BIO instrument (instrument field of view). Hence, one of the main drawbacks of this technology is this working distance between patient and examiner, because the area of interest (which is the image of the patient's fundus) is so small compared to the entire field of view through the instrument. What is needed in the art is a way to modify the examiner's view through the BIO instrument itself (instrument field of view), so that the image of the patient's fundus (condensing lens field of view) is magnified to fill a larger portion of the instrument field of view, allowing the finer fundus details to be seen more easily.

Each of the two oculars, or eyepieces, of the BIO into which the examiner peers or looks is separately adjustable to the examiner's inter-pupillary distance (hereinafter as "PD") to enable a binocular stereoscopic view of the fundus. The right and left oculars each have reflectors (e.g., mirrors) that form a horizontal periscope for each eye to reduce the examiner's PD so it is small enough to enable the examiner to see into the patient's eye with both of theirs simultaneously. This allows the examiner to obtain a binocular stereoscopic view of the patient's fundus. Without the mirrors in the right and left oculars, the angle between the examiner's eyes, as he or she looks through the patient's pupil, would be too great to be able to see the patch of illuminated fundus with both eyes at the same time.

The hand-held condensing lens creates an in-focus image of the fundus between the examiner and the hand-held condensing lens, typically located within a few inches of the condensing lens surface on the examiner's side of the hand-held condensing lens. Specifically, the hand-held condensing lens forms an image of the patient's fundus in real space out in front of the patient's eye. Due to the optics in the hand-held condensing lens, the fundus image seen by the examiner is inverted (upside-down and backwards). Conventional BIOs merely transfer this in-focus image to the examiner's eyes, with separately adjustable BIO oculars enabling the BIO to adapt to the examiner's particular PD. However, where a typical BIO merely views the image, the present invention magnifies what is seen in the instrument field of view, which also magnifies the fundus image produced by the condensing lens.

Different powered hand-held condensing lenses may be used in conjunction with the BIO. By using different powered hand-held condensing lenses, the examiner can change the magnification and visual field of view of the fundus produced by the hand-held condensing lens (condensing lens field of view). Given that the hand-held condensing lens is of a fixed diameter, only so much of the fundus image can fit inside. Currently, the examiner can switch to a lower powered hand-held condensing lens to produce a more magnified image of the fundus, but when he or she does so, the area of the fundus that can be seen in a single view becomes more limited (i.e., smaller condensing lens field of view). Conversely, if the examiner switches to a higher-powered hand-held condensing lens, the image formed by that hand-held condensing lens will show a broader view of the fundus (i.e., larger condensing lens field of view), but the image will be minified.

Lower powered hand-held condensing lenses form an image with greater fundus magnification, but a more restricted condensing lens field of view. Higher powered hand-held condensing lenses produce a larger condensing lens field of view, but with corresponding minification of the fundus image. Optically, as magnification increases, the visual field of view decreases. Therefore, while it is possible to make fundus details appear larger by switching to a lower powered hand-held condensing lens, the tradeoff is that only a smaller area of the fundus (condensing lens field of view) can be seen at any one time.

To see fundus details at increased magnification by switching condensing lens power (i.e., a lower power condensing lens), less fundus area can fit into the image produced by the hand-held condensing lens, resulting in a decreased condensing lens field of view. Further, the fundus image formed by the condensing lens takes up less than half (only about 40%) of the instrument field of view. Furthermore, in all these cases, the image of the fundus that the condensing lens forms is still approximately 50 mm in diameter, viewed at a working distance of approximately 50 cm from the examiner's eyes, and so does not fill the instrument field of view.

Magnification can also be increased by moving closer to an object being viewed so it subtends a larger visual angle, and thus appears larger. However, simply moving closer to the eye when using a BIO is problematic, in that in addition to forming the fundus image, the hand-held condensing lens is also focusing an image of the examiner's headset (e.g., consisting of the two oculars and the light source) in the patient's pupil. The closer the instrument gets to the hand-held condensing lens (and the patient's eye), the larger the image of the ophthalmoscope headset in the plane of the patient's pupil becomes, until the image is so large that it no longer fits within the patient's pupil at all. At this point, the examiner loses their binocular, stereoscopic view of the fundus.

Thus, there is a need in the art to develop novel and improved BIO systems including, but not limited to, advanced designs and methods of performing binocular indirect ophthalmoscopy that enable the examiner to obtain enhanced views of a patient's fundus.

SUMMARY OF THE INVENTION

The following is a summary of the invention in order to provide a basic understanding of some aspects of the invention. This summary is not intended to identify all key or critical elements of the invention or to delineate the entire scope of the invention. Its sole purpose is to present some concepts of the invention in a simplified form as a prelude to the more detailed description that is presented later.

Reference throughout this specification to "one embodiment" or "an embodiment" means that a particular feature, structure, or characteristic described in connection with an embodiment is included in at least one embodiment of claimed subject matter. Thus, appearances of phrases such as "in one embodiment" or "an embodiment" in various places throughout this specification are not necessarily all referring to the same embodiment. Furthermore, particular features, structures, or characteristics may be combined in one or more embodiments.

What is needed in the art is a way to magnify the fundus image produced by any hand-held condensing lens the examiner may choose to use (i.e., "condensing lens field of view") so that it fills more of the examiner's field of view through the BIO itself (i.e., the "instrument field of view"). Indeed, this comprises the essence of the present invention—the fact that it affects the instrument field of view and not the condensing lens field of view. This means that it can work with any condensing lens that may be preferred by an individual examiner.

The present invention accomplishes this by providing the BIO with a Galilean tele-microscope (hereinafter as "tele-microscope") attachment to the instrument's headset. In certain embodiments, the attachment is a tele-microscopic optic. The view of the fundus image (i.e., the condensing lens field of view), which is formed by the hand-held condensing lens will be enlarged by the tele-microscope no matter what power hand-held condensing lens is used. Consequently, different powered hand-held condensing lenses may still be used to either get more magnification or a larger visual field of view of the fundus, but the image the examiner views through the BIO with the tele-microscope attached will now take up about two thirds (or 67%) of his or hers view through the instrument (instrument field of view), instead of only less than half (about 40%) of the instrument field of view without the tele-microscope. Additionally, there will be less extraneous, distracting material in the instrument's field of view outside the condensing lens, further allowing the examiner to concentrate on the area of interest, which is the view of the fundus.

The present invention may be comprised of a permanently mounted tele-microscopic optic (e.g., attachment) or a detachable/removable tele-microscopic optic (e.g., clip-on, grip-on, screw-on, magnetic, or other suitable method of affixation) affixed to the front of an existing BIO headset. The tele-microscopic optic may be designed to flip, slide, or rotate (e.g., rotate up, rotate down, rotate away, or rotate to the side) out of the way of the viewing window to allow fundus viewing without the additional magnification provided by the tele-microscope, if desired. The tele-microscopic optic (e.g., attachment) is comprised of a self-contained tele-microscope, which magnifies the view of the hand-held condensing lens that the examiner holds in front of the patient's eye, within which he or she sees an image of the patient's fundus. The present invention provides this magnification without requiring any modifications to the existing BIO optics.

The working distance of the tele-microscope optic is set to allow the examiner to work at a suitable arm's length (approximately 50 cm), the same distance as without the tele-microscopic optic on the front of an existing BIO instrument. This design adds insignificant weight and size to conventional BIO instruments and can be fit to most existing models by merely changing the mount design by which the tele-microscope optic attaches to the BIO headset.

With conventional BIOS, greater magnification of the fundus image produced by the hand-held condensing lens can only be achieved by switching to a lower powered hand-held condensing lens. A +20 diopter (D) hand-held condensing lens is used most often for routine examination and is referred to herein as a "standard" powered hand-held condensing lens. A lower powered lens, such as a +14 D or a +15 D hand-held condensing lens, will produce a more magnified image relative to the "standard" +20 D hand-held condensing lens, but the condensing lens field of view that the examiner sees at any one time will be correspondingly decreased, as magnification and visual field of view are inversely related in optics. As such, a lower powered hand-held condensing lens provides increased magnification, but sacrifices condensing lens field of view. Further, while a higher-powered (typically about +25 D to +40 D) hand-held condensing lens provides a wider field of view of the fundus, the image formed will be minified or exhibit less magnification, as compared to a standard powered condensing lens.

By attaching a tele-microscope to the BIO headset, which magnifies the image produced by a condensing lens as seen by the examiner through the instrument (regardless of condensing lens power), the present invention achieves magnification similar to that produced by a lower-power hand-held condensing lens, while preserving the wider area of fundus (condensing lens field of view) observed with the "standard" powered hand-held condensing lens.

For the present invention, because the magnifying optics are attached immediately in front of the BIO headset, the magnification (instrument field of view) remains independent of the hand-held condensing lens power. With the condensing lens, and the fundus image created by it, being magnified by the improved BIO (with tele-microscope attachment) of the present invention, the condensing lens field of view for a hand-held condensing lens of any power remains the same as it would with any conventional BIO but appears magnified to the examiner.

As compared to the present invention, using a conventional BIO with a lower powered hand-held condensing lens would result in similar magnification, but with the examiner able to see less fundus area (i.e., smaller condensing lens field of view) in any given view.

These and other aspects of the present invention are realized in an improved BIO tele-microscopic optic and method of performing binocular indirect ophthalmoscopy, as shown and described in the following figures and related descriptions. Additional features and advantages of the invention will be set forth in the detailed description that follows, taken in conjunction with the accompanying drawings, which together illustrate by way of example, the features of the invention.

BRIEF DESCRIPTION OF THE DRAWINGS

Non-limiting and non-exhaustive features will be described with reference to the following figures, wherein like reference numerals refer to like parts throughout the various figures. The figures below were not intended to be drawn to any precise scale with respect to size, angular relationship, or relative position.

Various embodiments of the present invention are shown and described in reference to the numbered drawings wherein:

FIG. 7A-FIG. 7B depict images of an examiner's visual field of view through an unmodified BIO and the examiner's visual field of view with a magnifying attachment, where the fundus view takes up a much larger portion of the examiner's visual field of view.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed so as to enable one skilled in the art to practice the present invention. These, and other, aspects and objects of the present invention will be better appreciated and understood when considered in conjunction with the following description and the accompanying drawings.

It should be understood, however, that the following description, while indicating preferred embodiments of the present invention and numerous specific details thereof, is given by way of illustration and not of limitation. The drawings and following description are exemplary of various aspects of the invention and are not intended to narrow the scope of the appended claims.

Many changes and modifications may be made within the scope of the present invention without departing from the spirit thereof and the invention includes all such modifications. For instance, although the detailed description deals primarily with systems (e.g., a novel lens assembly) and methods directed to utilizing the systems to provide an improved BIO and improved performance of binocular indirect ophthalmoscopy, other configurations are contemplated using the details disclosed herein, such as: additional methods and means of mounting the optics to the BIO headset, or additional systems implementing a computer system and/or non-transitory computer readable media.

Figure 1:
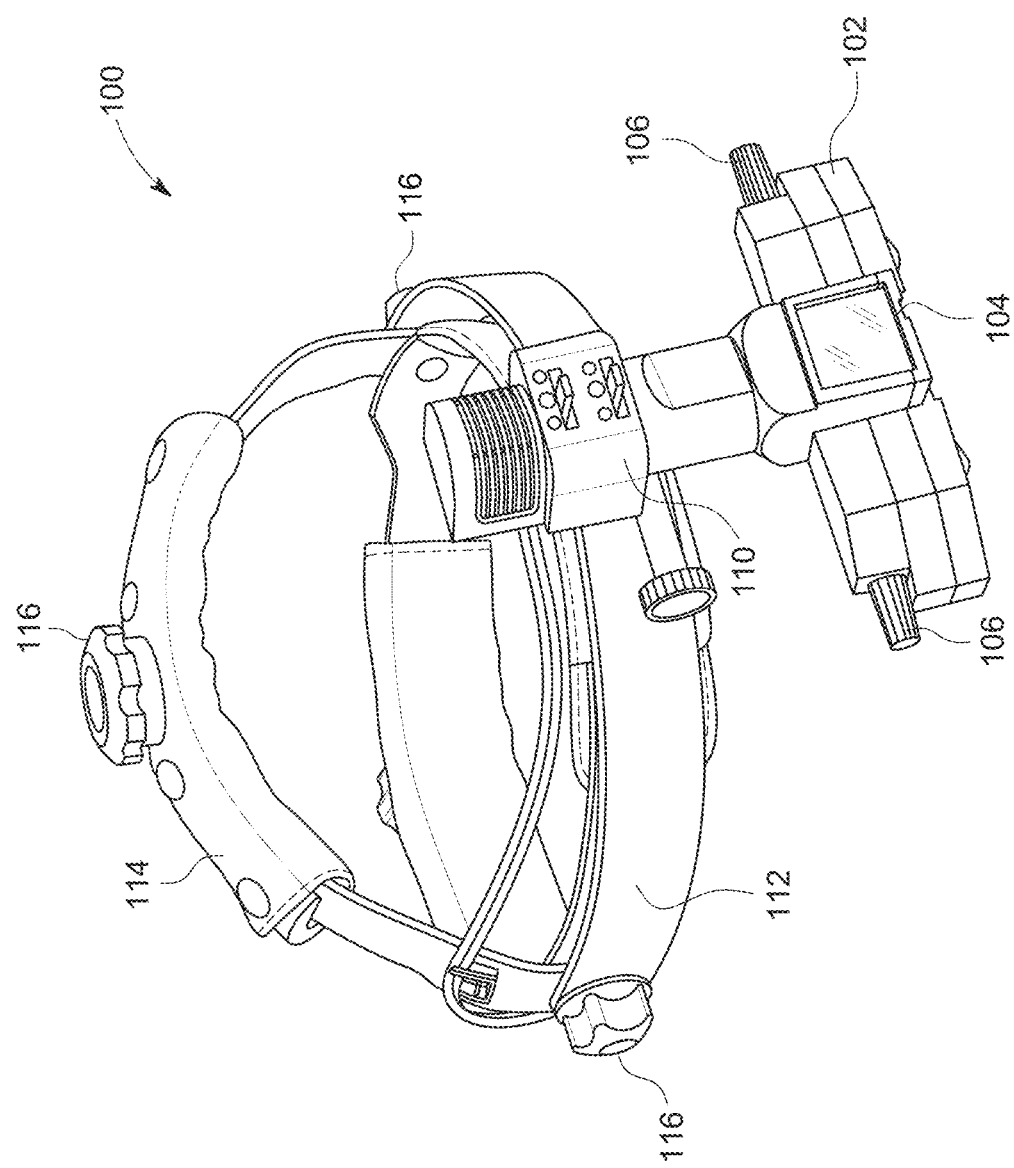
FIG. 1 depicts an image of a conventional BIO.

FIG. 1 depicts an image of a conventional BIO.

FIG. 1 illustrates a conventional BIO 100 of the prior art, which may be worn on a head of an examining ophthalmologist or optometrist (indicated as "examiner" herein). The BIO 100 may comprise a headset 102 (e.g., a BIO headset) that provides the examiner with a binocular view of the patient's fundus 122 (of FIG. 2). The headset 102 may additionally include a viewing window 104, an illumination mirror adjustment 106 (e.g., via a knob means, a dial means, or another means), and oculars 108 (of FIG. 2; an ocular lens (e.g., +2 D)). The headset 102 also typically includes a light source 110, a headband 112, an overband 114, and various band adjustments 116 (e.g., via the knobs means, the dials means, or the other means). The oculars (not shown) are located on the rear of the headset 102.

For a simple magnifier, the magnification M is calculated by this formula:

$$M = \text{Lens Power}/4$$

In a simple magnifier, magnification increases as lens power increases. However, for indirect ophthalmoscopy the condensing lens is not a simple magnifier, but rather is part of an optical system that includes the eye itself. This system can be described essentially the same as an astronomical telescope, but in reverse.

The magnification of a telescope is calculated by the following formula:

$$M=\text{Objective Lens Power/Ocular Lens Power}$$

With indirect ophthalmoscopy the examiner is actually looking through this telescope backwards, so the eye itself is the objective lens and the condensing lens is the ocular. Therefore, the formula becomes:

$$M=\text{Eye Power/Condensing Lens Power}$$

The power of the eye is usually taken to be 60 D. So being in the denominator, as condensing lens power increases, the magnification of this system decreases (and vice versa). This affects only the field of view produced by the condensing lens. In other words, the optics of the eye, in conjunction with the optics of the condensing lens, as well as the distance between the eye and the condensing lens, determines the condensing lens field of view and the magnification of the area of the fundus contained in the image created by the condensing lens.

Figure 2:
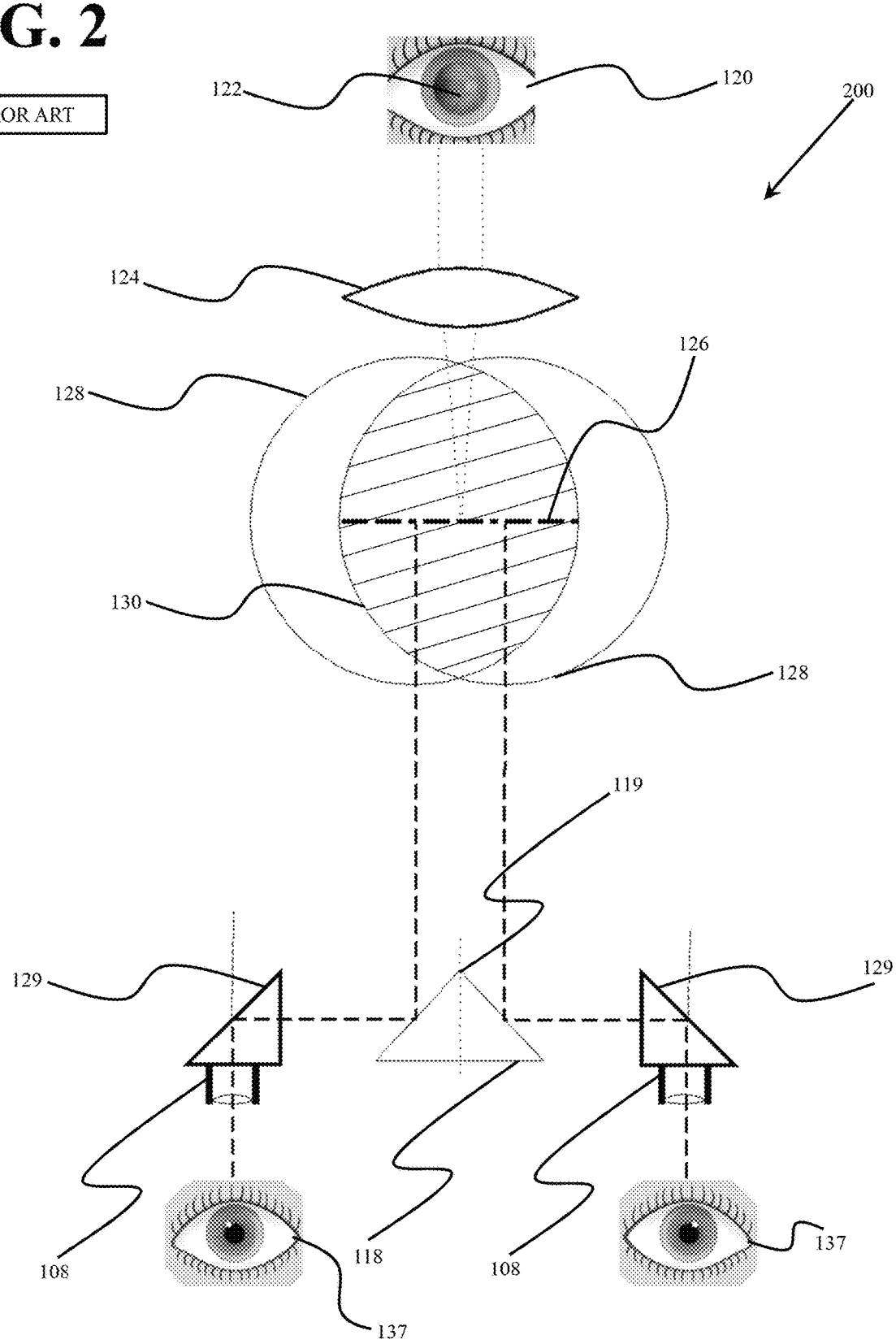
FIG. 2 depicts a schematic diagram of the optics found in a conventional BIO.

FIG. 2 depicts a schematic diagram of the optics found in a conventional BIO.

The schematic diagram 200 of FIG. 2 depicts the conventional BIO 100 (of FIG. 1). The schematic diagram 200 further illustrates the formation of an image 126 of the fundus 122 of a patient's eye 120 by the hand-held condensing lens 124 held by the examiner in front of the patient's eye 120.

The left and right oculars 108 of the BIO 100 are symmetric across the central mirror block 118. There are two mirrors 129, right and left, typically equal distance from the central mirror block 118 and used to reduce the examiner's PD so that it is small enough to enable the examiner to see the patient's illuminated fundus 122 with both of the examiner's eyes 137 at the same time (binocularly).

The central mirror block 118 splits the image 126 formed by the hand-held condensing lens 124 into left and right portions, bifurcated at the apex of the central mirror block 118 along a center line 119, meaning that the left and right sides of the central mirror block 118 respectively reflect unique portions of the image 126 formed by the hand-held condensing lens 124. Each side of the central mirror block 118 reflects the image from a somewhat laterally displaced perspective (i.e., laterally offset from the respective opposing side of the mirror block), thereby sending to the oculars 108 slightly offset fields of view 128 with a common overlapping visual field of view area 130 that enables the examiner to view the fundus image 126 with stereoscopic binocular vision. The image that the examiner views is that of the retina through the hand-held condensing lens 124 which is positioned at a working distance of about an arm's length (approximately 50 cm) from the examiner.

Figure 3:
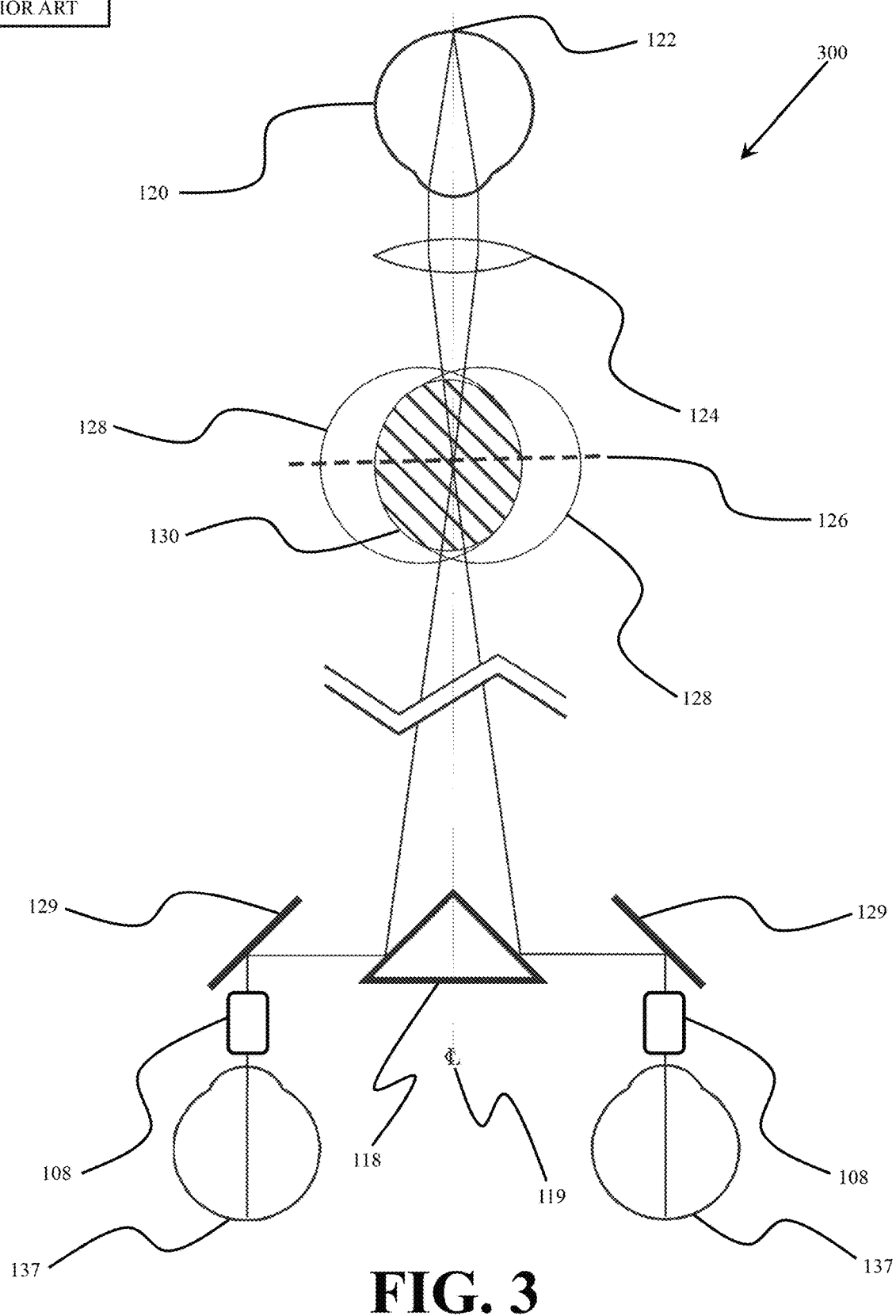
FIG. 3 depicts a schematic diagram of a viewing path of a conventional BIO.

FIG. 3 depicts a schematic diagram of a viewing path of a conventional BIO.

As illustrated in the schematic diagram 300 of the viewing path of the conventional BIO of FIG. 3, light coming out of a patient's eye 120 from the patient's fundus 122 is focused by the hand-held condensing lens 124 as a real, inverted, aerial image 126. A central mirror block 118 splits the image 126 formed by the hand-held condensing lens 124 into a right and a left portions, bifurcated at the apex of the central mirror block along on a center line 119. The right and left sides of the central mirror block 118 each reflect their own, somewhat laterally displaced, perspective of the fundus image 126 (i.e., laterally offset from the respective opposing side of the mirror block), which is then reflected by a mirror 129 into the ocular 108 and then into the examiner's eye 137 on the right and the left sides. The slightly offset fields of view 128 of the right and the left eyes have a common overlapping area 130, which allows the examiner to perceive a binocular stereoscopic view of the fundus image 126 that is formed by the hand-held condensing lens 124.

FIG. 4A-FIG. 4D depict a tele-microscopic optic (or attachment) that is mounted to a front of a BIO headset.

Figure 4A:
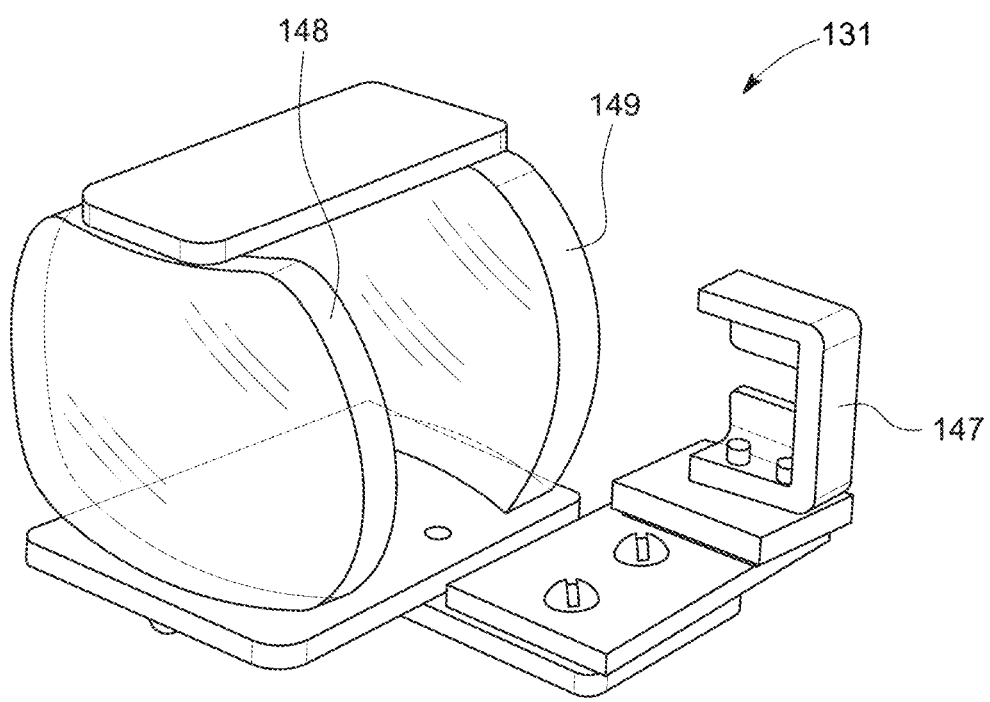
FIG. 4A-FIG. 4D depict a tele-microscopic optic (or attachment) that mounts to a front of a headset of a BIO.
Figure 4B:
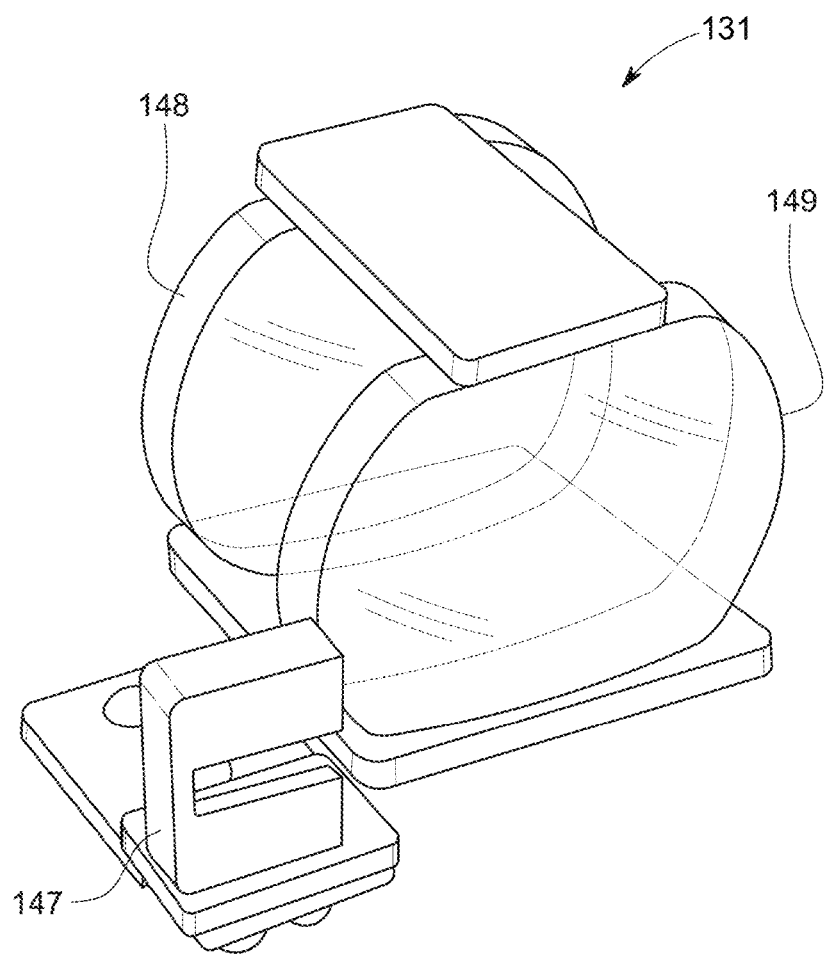

FIG. 4A displays the tele-microscopic optic 131 (i.e., the attachment). In some examples, the tele-microscopic optic 131 may be a removable/detachable attachment affixed to the front of the conventional BIO 100, via the headset 102. The tele-microscopic optic 131 may be a clip-on attachment, a grip-on attachment, a screw-on attachment, a magnetic attachment, or an attachment affixed to the conventional BIO 100 via another suitable method. The tele-microscopic optic 131 may be designed to flip, slide, rotate or otherwise move out of the way of the viewing window 104 (e.g., up, down, away, or to the side).

In other examples, the tele-microscopic optic 131 may be a permanent attachment or built into the headset 102. Further, the tele-microscopic optic 131 is a Galilean tele-microscope, comprised of two or more lenses, each of which may be comprised of a concave (plano-concave or bi-concave) lens form, a convex (plano-convex or bi-convex) lens form, a meniscus (positive meniscus or negative meniscus) lens form, or any combination thereof. Further, the design surfaces of the two or more lenses of the Galilean tele-microscope may include design surfaces selected from the group comprising: a spherical design, an aspheric design, and a combination thereof.

In some examples, the power of the objective lens 148 and the power of the ocular lens 149 may be the same power but opposite sign. The power of the objective lens 149 and the power of the ocular lens 149 may be in a range of approximately +/−2 diopter (D) to approximately +/−50 D. In a preferred embodiment, the power of the objective lens 149 and the power of the ocular lens 149 may be in the range of approximately +/−5 D to approximately +/−20 D. In other embodiments, the power of the objective lens 149 and the power of the ocular lens 149 may be in the range of approximately +/−5 D to approximately +/−15 D. In further embodiments, the power of the objective lens 149 and the power of the ocular lens 149 may be in the range of approximately +/−5 D to approximately +/−10 D. In other examples, the power of the objective lens 148 and the power of the ocular lens 149 may be of differing powers. In the current configuration contemplated, the objective lens 148 is approximately +10 D and is a meniscus lens. In the current configuration contemplated, the ocular lens 149 is approximately −10 D and is a meniscus lens.

Figure 4C:
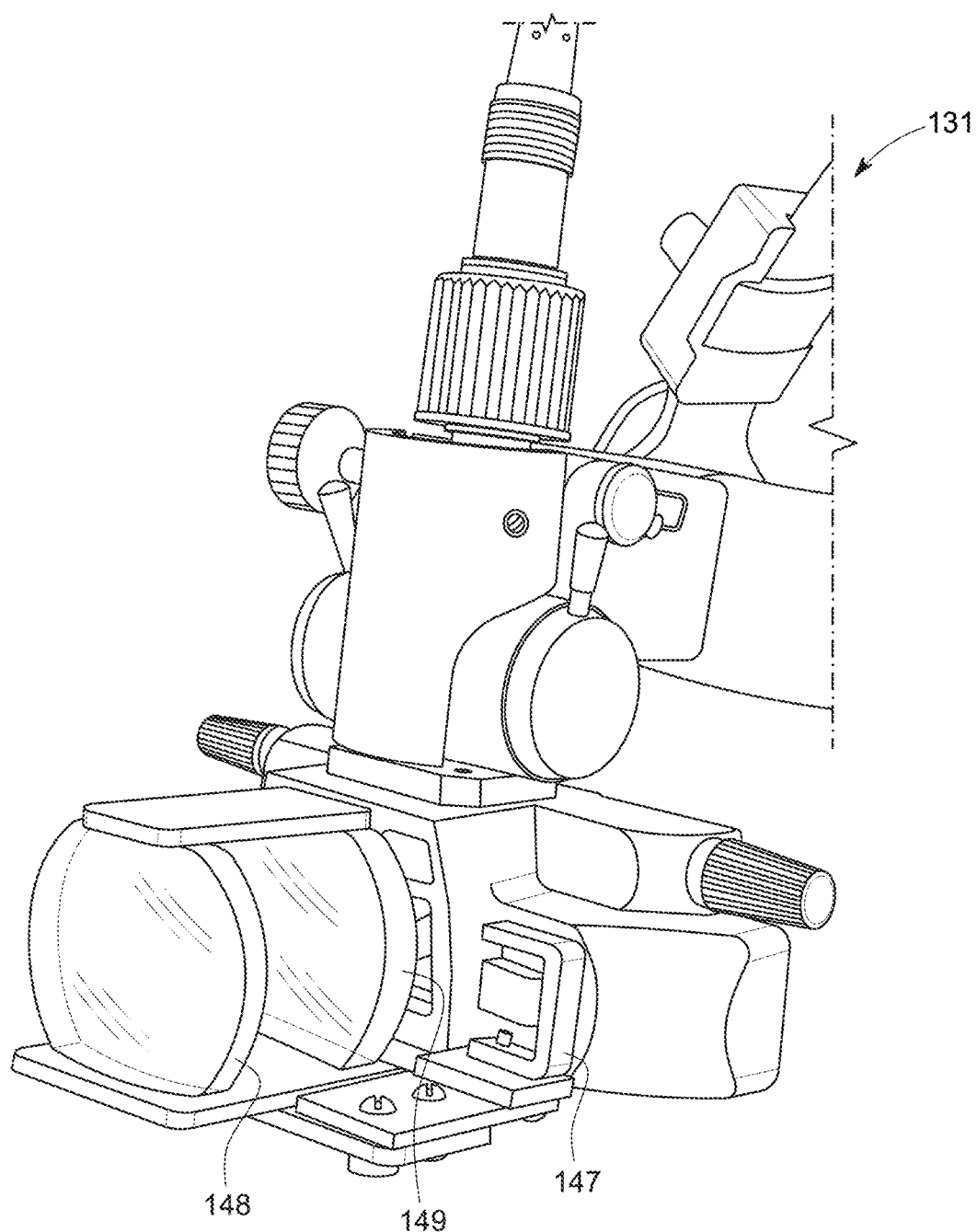
Figure 4D:
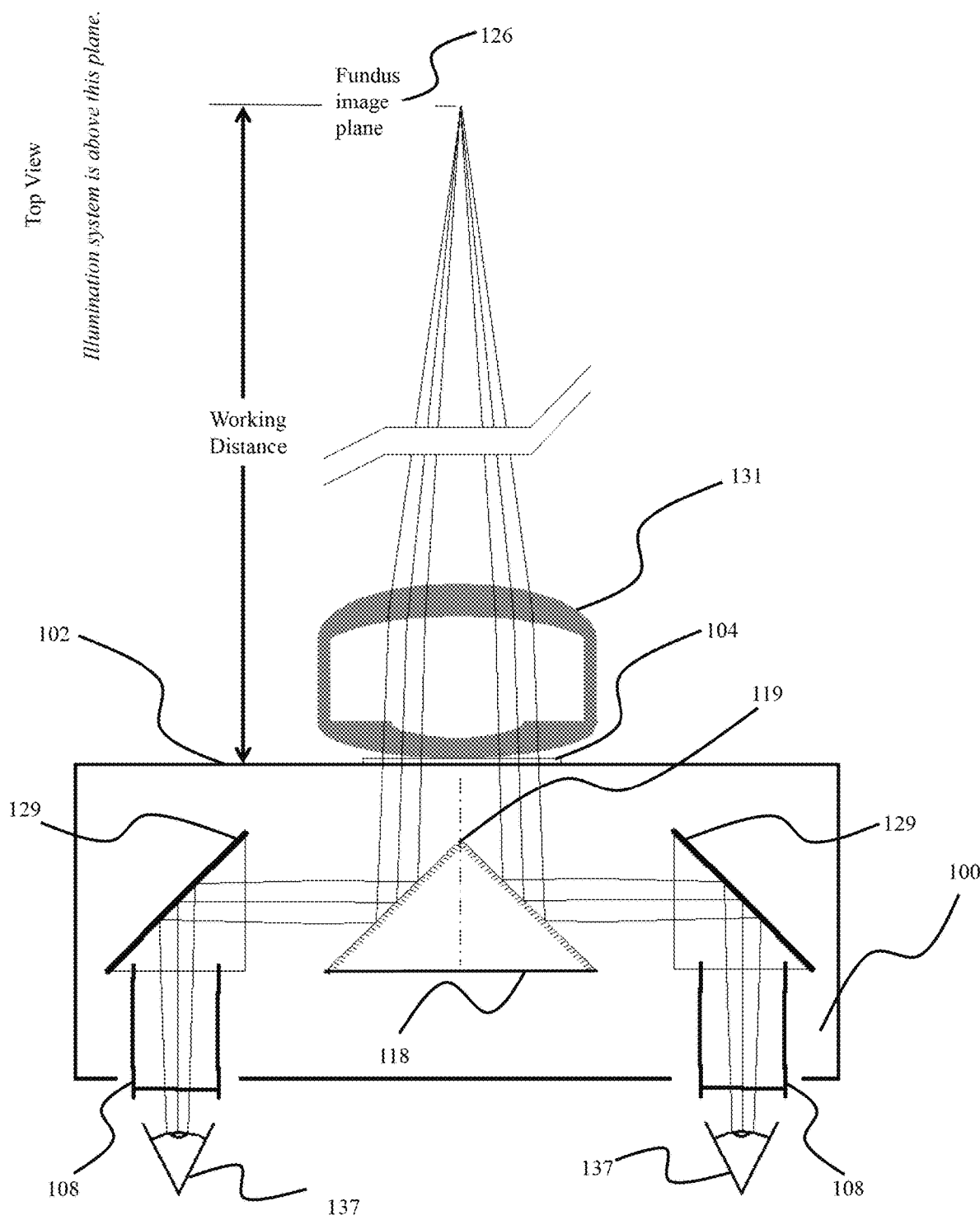

Moreover, the tele-microscopic optic 131 may be mounted to the front of the conventional BIO 100, via the headset 102, as shown in FIG. 4C, via a suitable mount 147. The mount may be further customized to fit individual models of conventional BIOs. Furthermore, as shown in FIG. 4D, the tele-microscopic optic 131, being in the front of the examiner's viewing path, magnifies the instrument field of view of the patient's fundus 122 formed at the plane of the fundus image 126 by the hand-held condensing lens, i.e., the condensing lens field of view.

In a preferred embodiment, the position of the objective lens of the tele-microscopic optic may be adjustable, allowing an examiner to focus on the fundus image and adjust their working distance for the examination. In one example the objective lens may be mounted on a slide mechanism with, for example and without limitation, an adjustable knob operative to move the objective lens longitudinally; closer or further distances from the ocular lens. Another example may use a telescopic lens housing, as is found in conventional camera lenses, enabling the examiner to rotate the telescoping fixture, to which the objective lens is mounted, and thereby increase or decrease the distance between the objective lens and the ocular lens. Preferred embodiments include a locking mechanism to lock in place the objective lens, following adjustment, to set a fixed focus and working distance for the examination so that these parameters cannot be inadvertently changed during the exam.

Figure 5:
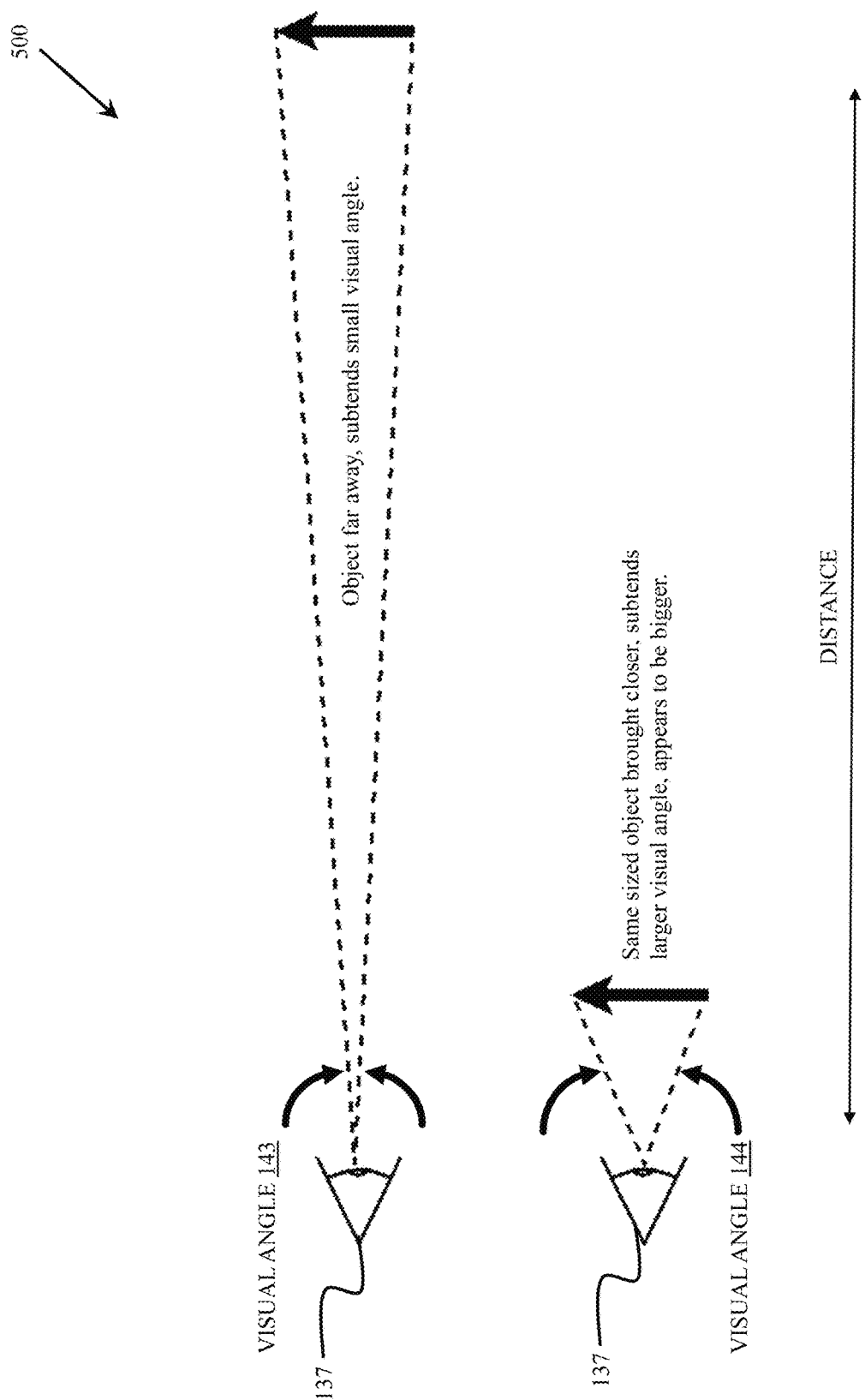
FIG. 5 depicts a schematic diagram illustrating the increased magnification gained by moving closer to an object, allowing it to subtend a greater visual angle and thus appear larger.

FIG. 5 depicts a schematic diagram illustrating the increased magnification gained by moving closer to an object, allowing it to subtend a greater visual angle and thus appear larger.

The schematic diagram 500 of FIG. 5 displays what occurs when the object (e.g., the patient's eye 120 of FIG. 2) is brought closer to the examiner's eye 137 (of FIG. 2). The closer the examiner's eye 137 is to the object, the larger visual angle 144 the examiner will see, thus making the image 126 appear larger. Additionally, the further the examiner's eye 137 is from the object, the smaller visual angle 143 the examiner will see, thus making the image appear smaller. It is important to note that the object never gets larger itself, rather it just appears larger because of the increased visual angle.

Figure 6:
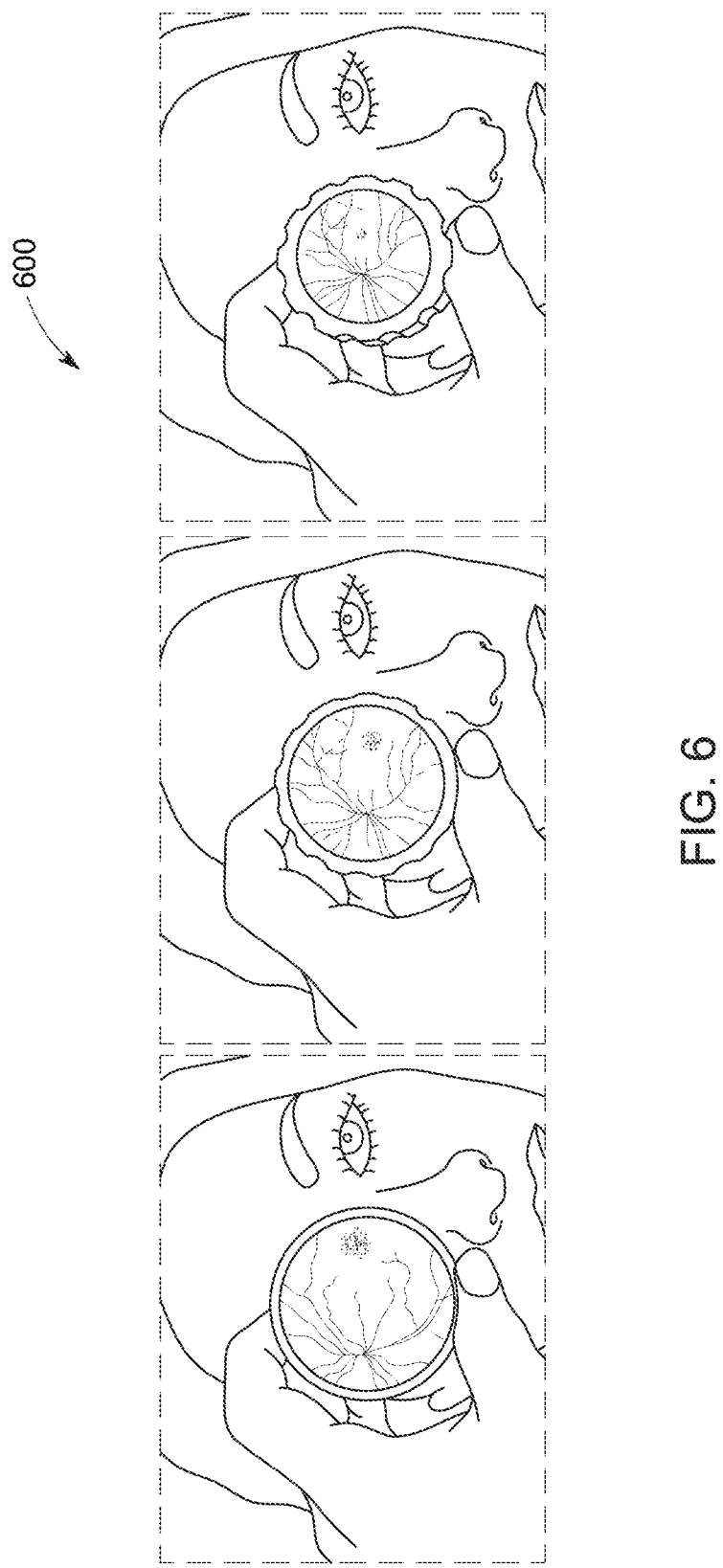
FIG. 6 depicts images of the examiner's view through an unmodified BIO using different powers of condensing lenses.

FIG. 6 depicts images of the examiner's view through an unmodified BIO using different powers of condensing lenses.

The images 600 of FIG. 6 display views through hand-held condensing lenses of differing powers. In the center is a picture of the view obtained with a "standard" +20 D condensing lens 124. A higher powered (e.g., +28 D) hand-held condensing lens 124 shows a larger condensing lens field of view, but at a decreased magnification (as shown on the right). On the left is a picture of the view obtained through a lower powered (e.g., +14 D) hand-held condensing lens 124, which gives a magnified view, at the expense of a smaller condensing lens field of view. Note that in all cases, the area of the examiner's visual field of view through the BIO taken up by the hand-held condensing lens 124 is quite small and is surrounded by extraneous material. In fact, very little of the examiner's visual field of view is taken up by the image of the fundus 122; most of the view is of anything but the fundus 122!

FIG. 7A and FIG. 7B depict images of an examiner's visual field of view through an unmodified BIO and the examiner's visual field of view with a magnifying attachment, wherein the fundus view takes up a much larger portion of the examiner's visual field of view through the instrument.

The image 700A of FIG. 7A depict the view through a conventional, unmodified BIO 100. The image 700B of FIG. 7B depicts the view through the present invention attached to the same BIO. The examiner is interested in viewing only what is seen within the hand-held condensing lens 124 in the center of the instrument's visual field of view, which has the fundus image 126 contained within it. The hand-held condensing lens 124 only takes about ~40% of the examiner's total instrument visual field of view in a "conventional" BIO, while it takes up approximately ~67% of the examiner's total instrument visual field of view obtained by the present invention. Therefore, finer fundus 122 details can be appreciated via the method of examination employing the present invention, as shown in FIG. 7B. Thus, the present invention magnifies the instrument field of view and is independent of the image produced by the condensing lens.

Figure 8A:
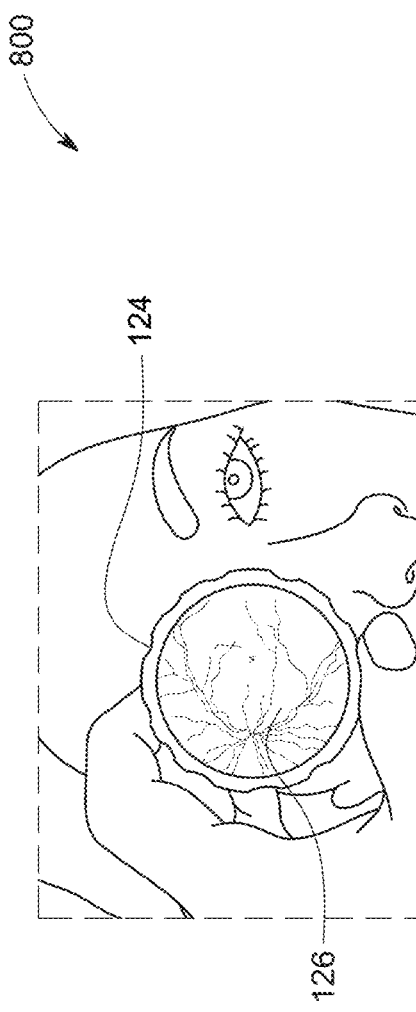
FIG. 8A-FIG. 8C depict images of a comparison of an examiner's field of view through a BIO with and without the magnifying attachment, showing the distracting, extraneous image content surrounding the fundus image that normally takes up a significant portion of the instrument field of view, much of which is eliminated from the examiner's view by the tele-microscopic magnifying attachment of the present invention.
Figure 8C:
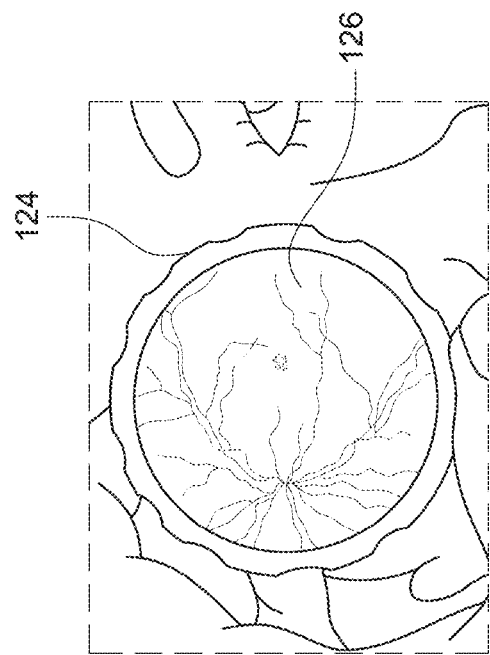
Figure 8B:
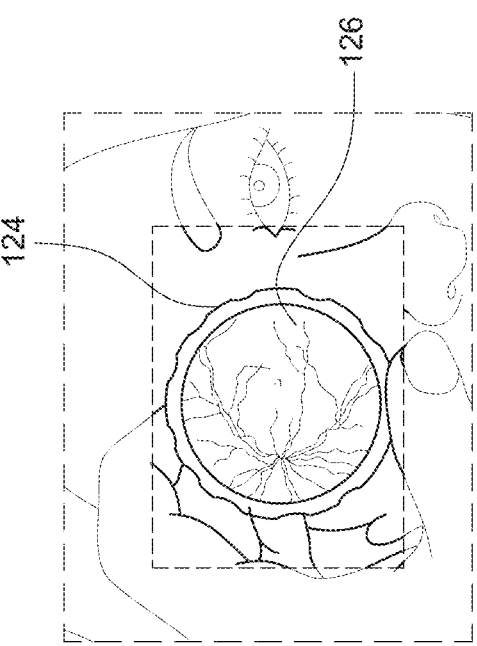

FIG. 8A-FIG. 8C depict images of a comparison of an examiner's field of view through a BIO with and without the magnifying attachment, indicating the extraneous material normally taking up a large portion of the examiner's field of view that is eliminated from the examiner's field of view by the magnifying attachment.

The images 800 of FIG. 8A-FIG. 8C display the problem associated with a conventional BIO 100, the hand-held condensing lens 124 only takes up a small portion of the examiner's visual field of view (i.e., instrument field of view), making it challenging to see fine detail. FIG. 8A shows an instrument field of view through a conventional BIO 100, with no magnification, as he or she examines the patient's fundus 122. With no magnification, the instrument field of view is cluttered with extraneous material making it difficult to see the fine details of the fundus 122. In FIG. 8B, the extraneous material is cut away, allowing the hand-held condensing lens 124 to take up more of the instrument field of view. FIG. 8C shows the instrument field of view through the same model BIO 100, but it is now modified with the tele-microscopic optic 131 (i.e., attachment). Here, the examiner sees the fundus 122 magnified, but at a regular working distance which enables the examiner to maintain a binocular, stereoscopic view of the patient's fundus. This allows finer fundus details to be observed.

Figure 9:
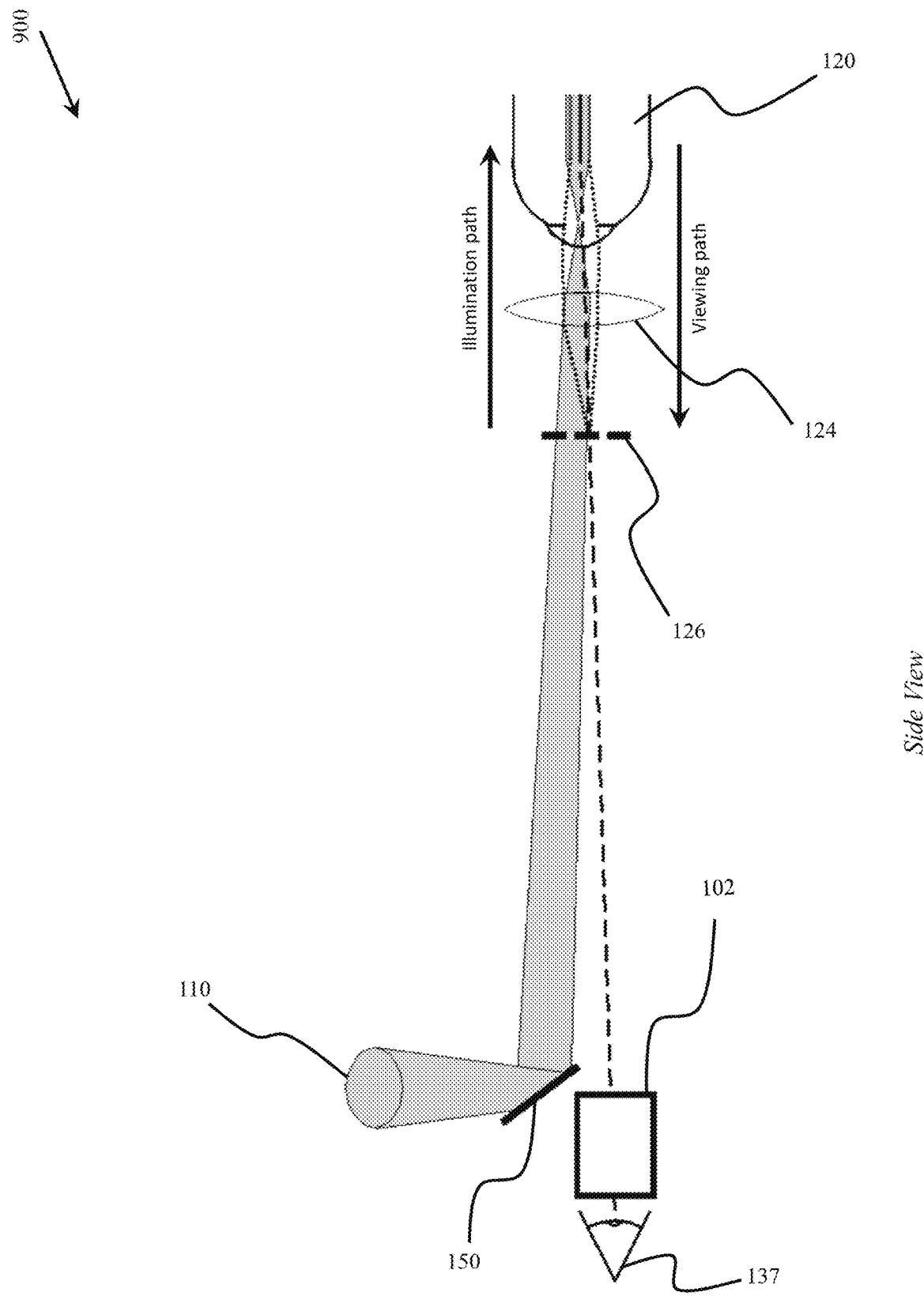
FIG. 9 depicts a diagram of the illumination light path of a conventional BIO.

FIG. 9 depicts a diagram of the illumination light path of a conventional BIO.

The diagram 900 of FIG. 9 shows the illumination light path of a light source 110 of a conventional BIO 100 during examination. The light is directed to an adjustable mirror 150, where it is reflected into the patient's eye 120 to illuminate it. As the light is being directed to the patient's eye 120, the hand-held condensing lens 124 focuses it through the patient's pupil to illuminate the inside of the patient's eye.

Figure 10:
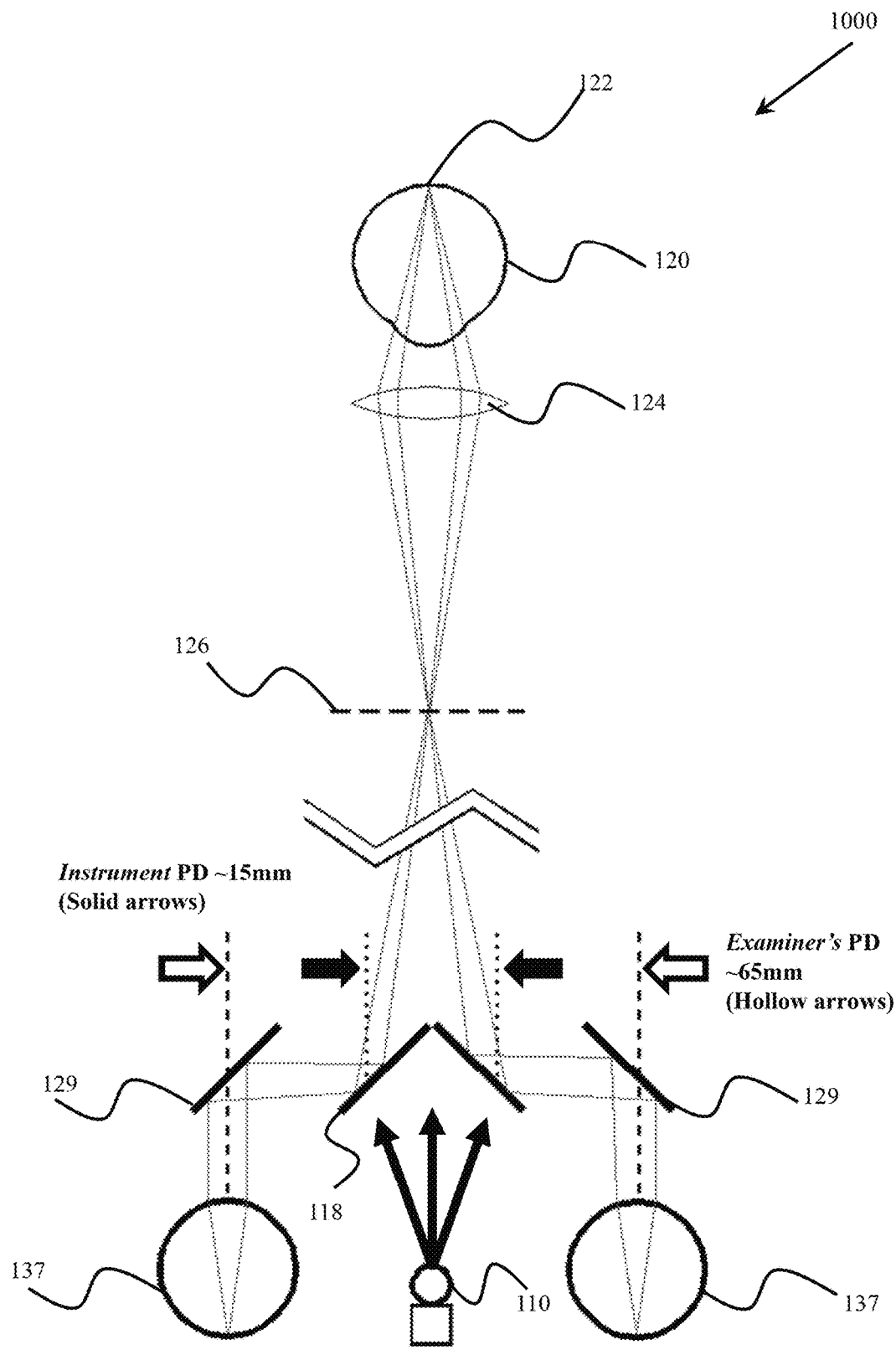
FIG. 10 depicts a diagram of the viewing system light path of a conventional BIO.

FIG. 10 depicts a diagram of the viewing system light path of a conventional BIO.

The diagram 1000 of FIG. 10 displays the viewing system's light path, which is directed from the patient's eye 120 by the central mirror block 118 and the left and right mirrors 129 to the examiner's eyes 137, effectively reducing the examiner's PD, allowing the examiner to obtain a line of sight very close to the illumination light's path so the examiner can see the area of the fundus 122 that is being illuminated with both eyes simultaneously. As previously explained, each side of the central mirror block 118 reflects the image 126 from a somewhat laterally displaced perspective (i.e., laterally offset from the respective opposing side of the mirror block), thereby sending to the oculars 108 slightly offset fields of view 128 with a common overlapping visual field of view area 130 (of FIG. 2) that enables the examiner to view the fundus image 126 with stereoscopic binocular vision. Further, while the examiner is at the working distance of an arm's length from the patient, the examiner may view the image of the patient's retina 126 in free space.

Figure 11:
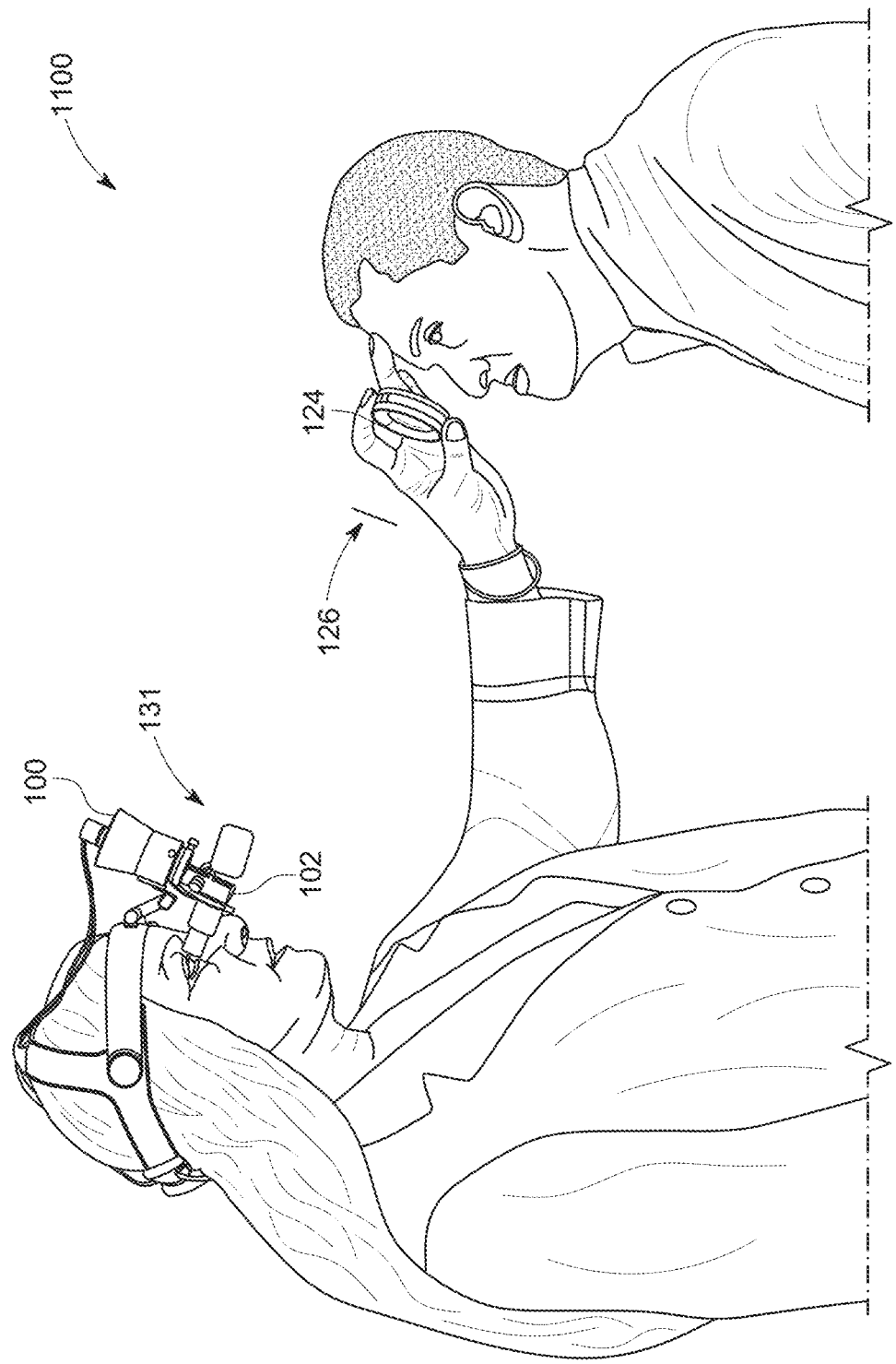
FIG. 11 depicts an image of an examiner performing binocular indirect ophthalmoscopy on a patient.

FIG. 11 depicts an image of an examiner performing binocular indirect ophthalmoscopy on a patient.

FIG. 11 depicts the image 1100 of the examiner performing binocular indirect ophthalmoscopy on a patient. During the exam, the examiner utilizes the conventional BIO 100. The tele-microscopic optic 131 (i.e., the attachment) is mounted to a front of the headset 102 (i.e., a BIO headset). The examiner also holds the hand-held condensing lens 124 at about (their) arm's length, just in front of the patient's eye, to view the image of the patient's fundus 122. The position of the real, inverted, aerial fundus image produced by the hand-held condensing lens 124 is also shown. The fundus image 126 may be formed at a location in space.

Figure 12:
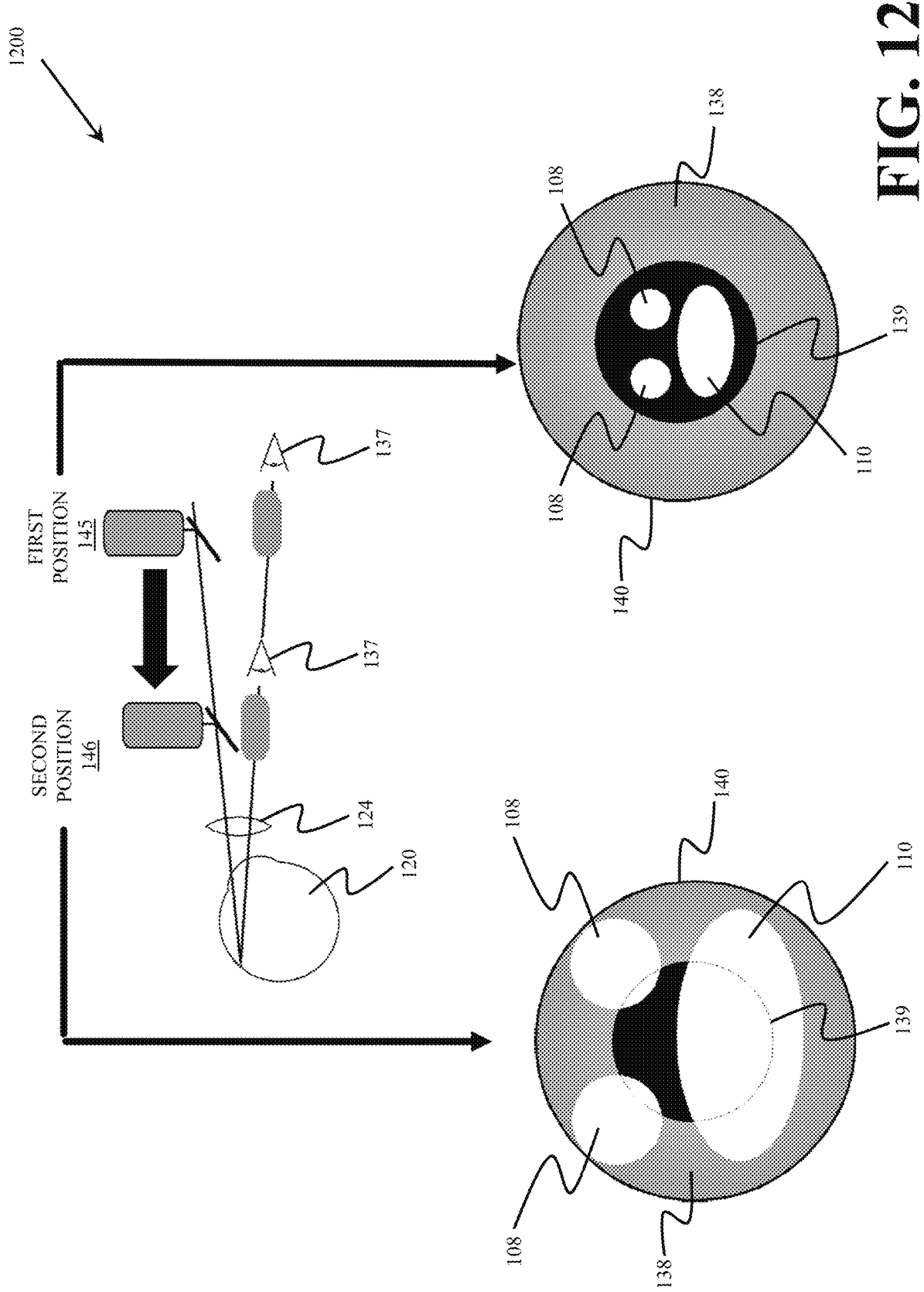
FIG. 12 depicts a schematic diagram illustrating the difficulty of decreasing an examiner's working distance to increase the visual size of a fundus view when performing binocular indirect ophthalmoscopy.

FIG. 12 depicts a schematic diagram illustrating the difficulty of decreasing an examiner's working distance to increase the visual size of a fundus view when performing binocular indirect ophthalmoscopy.

The schematic diagram 1200 is shown in FIG. 12, which displays the difficulty involved in simply decreasing the examiner's working distance in order to increase the visual size of the fundus view when performing binocular indirect ophthalmoscopy. The examiner's hand-held condensing lens 124 forms an image of the BIO's headset 102 in the patient's pupil 139. The patient's pupil 139 is surrounded by the patient's iris 138, which is surrounded by the corneal limbus 140. In the first position 145, the examiner holds the hand-held condensing lens 124 near the patient's eye 120 at one arm's length from the BIO headset (e.g., the "normal working distance"). At this distance, the hand-held condensing lens is able to image the entire BIO headset 102 (consisting of both oculars 108 and the light source 110) within the patient's pupil 139. Furthermore, the examiner is able to see the patient's fundus 122 in a good binocular, stereoscopic view.

As the examiner moves closer, to the second position 146, the image of the BIO's headset 102 (consisting of both oculars 108 and the light source 110) formed in the patient's pupil 139 by the hand-held condensing lens 124 becomes larger, and eventually becomes too large to be fully imaged in the patient's pupil 139. In this case, it becomes difficult to obtain and keep a binocular stereoscopic view of the image of the patient's fundus 126, and the image is disrupted by glare because the light source 110 is now partially illuminating and reflecting from the patient's iris 138. Therefore, simply moving closer will angularly magnify the image as shown in FIG. 5, but doing so will not improve the view of the fundus (i.e., condensing lens field of view), in part because both oculars 108 and the light source 110 cannot be imaged within the patient's pupil, and in part due to interference by glare reflecting from the patient's iris, among other factors.

Figure 13:
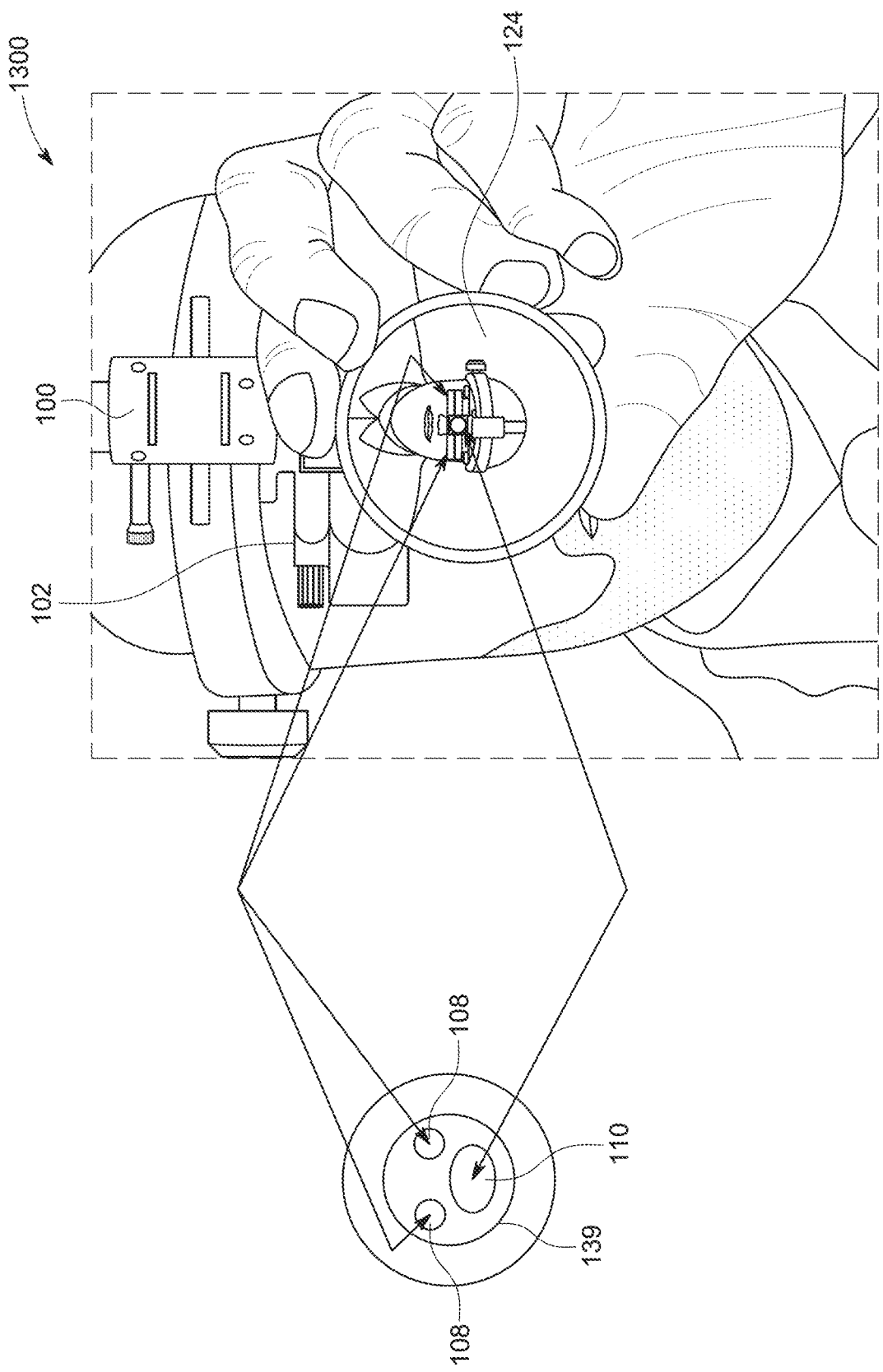
FIG. 13 depicts an image of the BIO from a patient's perspective, an image of a headset's ocular lenses and light source formed in the patient's pupil by the hand-held condensing lens.

FIG. 13 depicts an image of the BIO from a patient's perspective, an image of a headset's two or more ocular lenses and light source formed in the patient's pupil by the hand-held condensing lens.

FIG. 13 displays the image 1300 of the BIO from a patient's perspective. In the image 1300, the examiner's headset 102 is imaged in the patient's pupil 139, by the hand-held condensing lens 124. Both oculars 108 and the illumination light 110 must be imaged fully within the patent's pupil 139 to obtain and maintain a binocular stereoscopic view of the patient's fundus.

With a conventional BIO, the hand-held condensing lens 124 (within which the examiner sees the image of the fundus 126 produced by the condensing lens, i.e., the condensing lens field of view) only takes up less than half of the instrument field of view (about 40%). This device magnifies the hand-held condensing lens 124 (and hence also the fundus image 126 produced by the hand-held condensing lens 124 that is viewed by the examiner) so that it fills a larger portion of the instrument field of view (now about 67%). Accordingly, any power condensing lens can be used without additional modification, allowing the advantages of different condensing lenses to be freely realized in conjunction with the present invention.

Consequently, it is possible to use a higher power (e.g., +28 D) hand-held condensing lens 124 to obtain a wider condensing lens field of view, while keeping the magnification similar to that provided by a "standard" +20 D hand-held condensing lens. Likewise, it is possible to use a "standard" (e.g., +20 D) hand-held condensing lens 124 to obtain higher magnification, such as that produced by a lower power (e.g., +14 D) hand-held condensing lens 124, while retaining the larger field of view similar to that provided by the "standard" +20 D hand-held condensing lens 124.

While it is true that increased magnification can only be achieved at the cost of a reduced field of view, by putting the magnifying optics immediately in front of the BIO headset 102, it is the instrument's field of view that is decreased rather than the condensing lens field of view. The only part of the view through the instrument (instrument field of view) that is lost is that which lies outside the periphery of the hand-held condensing lens 124 (and fundus image 126 produced by the hand-held condensing lens 124 that the examiner sees within it), which is irrelevant and of no value or interest when performing fundoscopy. The exclusion of this extraneous, peripheral portion of the image advantageously serves to concentrate the examiner's view on the fundus area observed. The instrument field of view is actually smaller, which eliminates all the peripheral extraneous material usually seen by an examiner within a conventional BIO field of view.

Binocular indirect ophthalmoscopy is typically performed by an examiner wearing a headset 102 that incorporates a light source 110 and a viewing system with reflectors. It is used to view the real, aerial image of a patient's fundus 126 produced by a hand-held condensing lens 124 held by the examiner in front of the patient's eye 120. The first reflectors (i.e., the central mirror block 118 of FIG. 4D), effectively reduce the examiner's PD and receive the incident rays from the entire image, which is visible only within a narrow angle about the hand-held condensing lens 124 axis.

The second reflectors (i.e., the two mirrors 129 of FIG. 4D) redirect the rays to the examiner's eyes 137 with the assemblies set to the examiner's PD. In some examples, the second reflectors may be prisms. The examiner adjusts the hand-held condensing lens 124 distance from the patient's eye 120 so that the fundus image 126 produced by the hand-held condensing lens 124 appears to fill the entire approximately 50 mm diameter hand-held condensing lens 124. The diameter of the hand-held condensing lenses are not limited to the diameters described herein and may, in some examples, vary in diameter by power and manufacturer.

However, with conventional BIOS, the hand-held condensing lens 124 does not completely fill the examiner's visual field of view through the instrument (instrument field of view). Typically, the examiner's hands, part of the patient's face, and other things are also seen through the instrument, all of which are irrelevant and distracting to the examination. By mounting a tele-microscope in front of the existing BIO headset, the image of the hand-held condensing lens 124 is enlarged to fill more of the examiner's visual field of view (instrument field of view) at the usual working distance, a distance at which the examiner is best able to keep and maintain a binocular stereoscopic view of the patient's fundus 122. By magnifying instrument field of view, it thus provides a magnified view of the fundus image 126 produced by the hand-held condensing lens, allowing finer anatomical detail to be seen over a larger area of the fundus than would otherwise be possible by just switching to a different powered condensing lens. This may obviate the need to resort to other or additional examination techniques.

A preferred embodiment of the present invention places an entire self-contained tele-microscope in front of the viewing window of a conventional BIO headset, rather than building the tele-microscope into the BIO headset itself, which could increase the complexity (and cost) of the viewing optics. The tele-microscopic optic may be a permanent attachment or a removable/detachable attachment. As a removable/detachable attachment, the tele-microscopic optic may flip, slide, rotate or otherwise move out of the line of sight (e.g., up, down, to the side, away), or otherwise removed from the examiner's line of sight—to provide conventional BIO examining capability, if desired. Further, the mount 147 is capable of being customized for individual BIOs based on the make and model. Additionally, the mount 147 may be permanently attached or the optics may be directly incorporated into the BIO headset design.

By using the tele-microscope of Galilean design instead of an astronomical design or a simple magnifier, this tele-microscopic optic magnifies the examiner's view through the instrument, while adding minimal weight, cost, and complexity. It keeps the working distance the same as that of a conventional BIO, which allows the hand-held condensing lens 124 to continue to project or image both oculars along with the light from the examiner's headset 102 completely within the patient's pupil 139, allowing a full binocular stereoscopic view of the patient's fundus 122 to be realized.

It should be understood that, although certain specific embodiments have just been described, claimed subject matter is not intended to be limited in scope to any particular embodiment or implementation. For example, the present invention may include other means or mechanisms of attachment and other means or mechanisms of mounting the optics assembly to the conventional BIO. Other methods of implementing the tele-magnifier system into the conventional BIO may be contemplated in additional embodiments. In further embodiments, differing shapes and sizes for the attachment of the tele-magnifier system may be contemplated.

It is appreciated herein that reference to a "patient's eye" may refer to either a human eye or an animal eye. As such, in additional embodiments, methods incorporating use of the tele-magnifier system for the examination of animals may be contemplated. For example, as the tele-magnifier system is light-weight, this system is ideal for use by veterinarians, who examine the eyes and ocular fundus of domestic and wild animals who may be unable to keep their eyes from moving.

In other embodiments, the tele-magnifier system may be used in conjunction with a computing device (e.g., a smartphone, a desktop computer, a laptop computer, a handheld tablet, etc.). In some examples, the tele-magnifier system may be an adapter affixed to or configured to interact with the computing device.

The computing device may include, among other components or engines, one or more sensors, two or more lenses, and an analysis application. In an example, the one or more sensors may identify a location of an ocular fundus on a human eye, an eye of an animal, or on a model of a human or animal eye. The two or more lenses of the tele-magnifier system may capture an image of the ocular fundus. Further, the analysis application may transmit the image of the ocular fundus to: another application on the computing device, another computing device, or a service for analysis.

Figure 14:
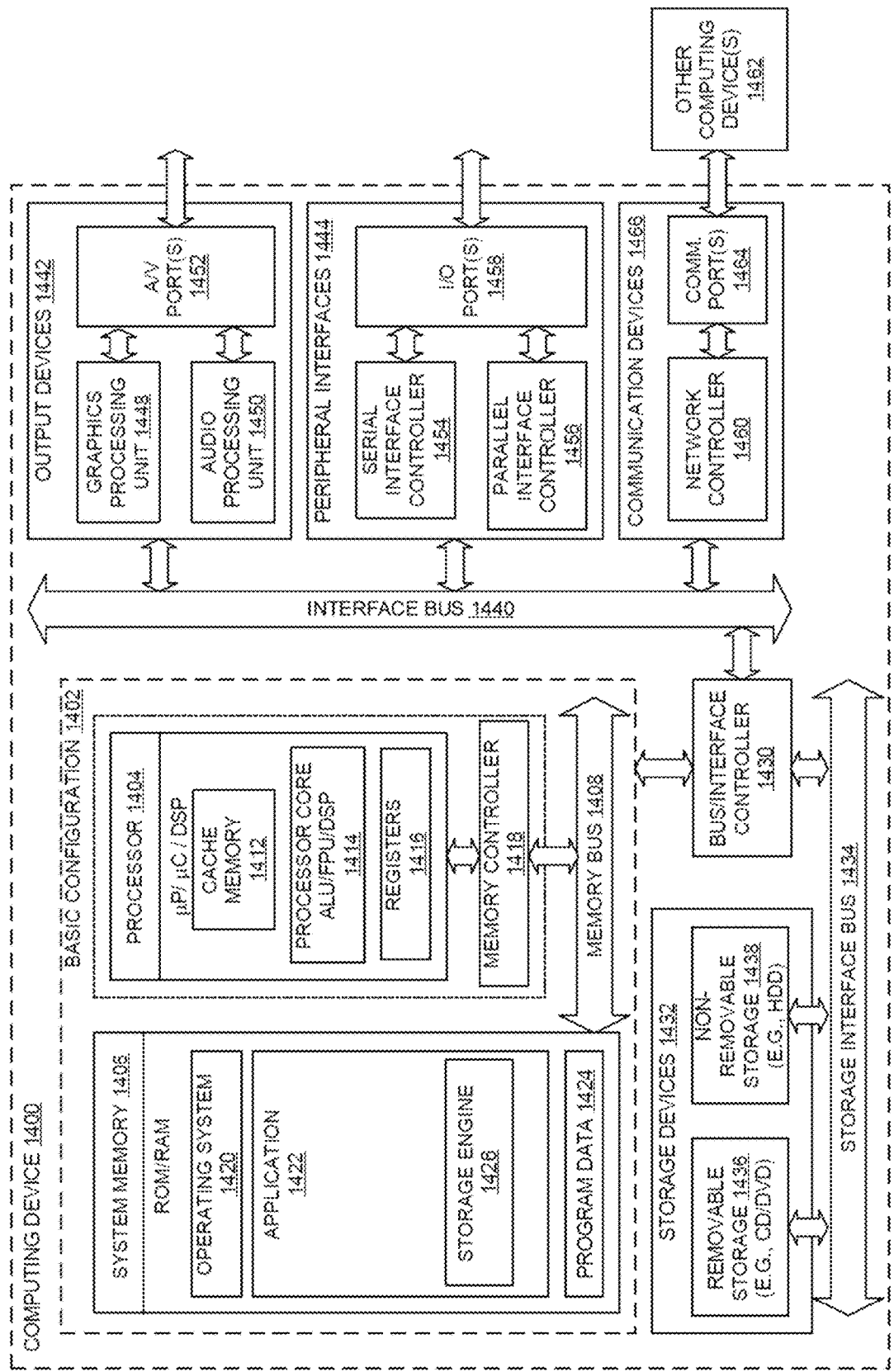
FIG. 14 depicts a block diagram of a computing device that may be used in accordance with the improved BIO system.

FIG. 14 depicts a block diagram of a computing device that may be used in accordance with the improved BIO system.

In some embodiments, the present invention may be a system, a method, a service, a computer system, and/or a computer program product. In an example, basic configuration 1402, the computing device 1400 includes one or more processors 1404 and a system memory 1406. A memory bus 1408 is used for communicating between the processor 1404 and the system memory 1406. The basic configuration 1402 is illustrated in FIG. 14 by those components within the inner dashed line.

Depending on the desired configuration, the processor 1404 may be of any type, including but not limited to a microprocessor (µP), a microcontroller (µC), a digital signal processor (DSP), or any combination thereof. The processor 1404 may include one more levels of caching, such as a level cache memory 1412, an example processor core 1414, and registers 1416, among other examples. The example processor core 1414 may include an arithmetic logic unit (ALU), a floating-point unit (FPU), a digital signal processing core (DSP Core), or any combination thereof. An example memory controller 1418 is used with the processor 1404, or in some implementations, the example memory controller 1418 is an internal part of the processor 1404.

Depending on the desired configuration, the system memory 1406 may be of any type, including but not limited to, volatile memory (such as RAM), non-volatile memory (such as ROM, flash memory, etc.) or any combination thereof. The system memory 1406 includes an operating system 1420, one or more applications, such as an application 1422, and program data 1424.

In an alternative embodiment, the present invention comprises a computer system including: A) one or more processors configured to execute one or more sensors and an analysis application; B) one or more memories; and C) one or more computer-readable hardware storage devices, wherein the one or more computer-readable hardware storage devices contain program code executable by the one or more processors via the one or more memories to implement a method to capture an image of an ocular fundus of a patient.

The method to computer system implemented method to capture an image of an ocular fundus of a patient may comprise the following steps: 1) detecting, a location of an ocular fundus using the one or more sensors; and 2) capturing via the one or more sensors, an image of the ocular fundus. In addition, the method implemented by the computer system may also comprise the step of 3) transmitting via the analysis application, an image of the ocular fundus to another computer system for analysis. Further, the location of the ocular fundus may be included or represented on an ocular fundus model of a patient and the image of the ocular fundus is a three-dimensional image.

In an example, the improved BIO system described herein may be used in the field of virtual reality. In an illustrative example, a user may place and affix a headset (e.g., a virtual reality headset) onto their head via numerous means. The user may also hold a computing device 1400 in their hand. The computing device 1400 may simulate a condensing lens.

In another alternative embodiment, the present invention may comprise a virtual reality system configured to capture an image of an ocular fundus of a patient. This virtual reality system comprises 1) a headset affixed to a head of a user; a computing device containing one or more sensors and an analysis application, wherein the computing device is held in a hand of the user. In addition, the computing device may further be configured to identify a location of an ocular fundus and capture an image of the ocular fundus using the one or more sensors.

In such virtual reality-based embodiments, the computing device may be further configured to simulate an ocular lens, and also to transmit, via the analysis application, the image of the ocular fundus to another computing device for analysis. Furthermore, the location of the ocular fundus may be included or represented on an ocular fundus model of a patient and the image of the ocular fundus is a three-dimensional image.

In another example, the improved BIO system described herein may be used in the conjunction with a computing device (e.g., a smartphone, a desktop computer, a laptop computer, a handheld tablet, etc.). The computing device 1400 may include, among additional modules/engines, one or more sensors and an application 1422 (e.g., an analysis application). The one or more sensors may be configured to identify a location of the ocular fundus. In some examples, the ocular fundus may be located on an ocular fundus model. The one or more sensors may additionally be configured to capture an image of the ocular fundus. Then, the application 1422 (e.g., the analysis application) may store the image of the ocular fundus in a storage engine 1426 associated with the application 1422. In some embodiments, the application 1422 (e.g., the analysis application) may then transmit the image of the ocular fundus to: another application on the computing device, another computing device, or a service for analysis.

The computing device 1400 may have additional features or functionality, and additional interfaces to facilitate communications between the basic configuration 1402 and any desired devices and interfaces. For example, a bus/interface controller 1430 is used to facilitate communications between the basic configuration 1402 and data storage devices 1432 via a storage interface bus 1434. The data storage devices 1432 may be one or more removable storage devices 1436, one or more non-removable storage devices 1438, or a combination thereof. Examples of the removable storage devices and the non-removable storage devices include: magnetic disk devices (e.g., flexible disk drives and hard-disk drives (HDD)), optical disk drives (e.g., compact disk (CD) drives or digital versatile disk (DVD) drives), solid state drives (SSD), and tape drives, among others. Example computer-readable storage media include volatile and non-volatile, removable and non-removable media implemented in any method or technology for the storage of information, such as computer-readable instructions, data structures, program modules, or other data.

In some embodiments, an interface bus 1440 facilitates communication from various interface devices (e.g., one or more output devices 1442, one or more peripheral interfaces 1444, and one or more communication devices 1466) to the basic configuration 1402 via the bus/interface controller 1430. Some of the one or more output devices 1442 include a graphics processing unit 1448 and an audio processing unit 1450, which are configured to communicate to various external devices, such as a display or speakers, via one or more A/V ports 1452. The one or more peripheral interfaces 1444 include a serial interface controller 1454 or a parallel interface controller 1456, which are configured to communicate with external devices, such as input devices (e.g., keyboard, mouse, pen, voice input device, touch input device, etc.) or other peripheral devices (e.g., printer, scanner, etc.) via one or more input/output (I/O) ports 1458. The one or more I/O ports 1458 may allow for varying means of connection to external devices, such as via a Universal Serial Bus (USB). An example of the one or more communication devices 1466 include a network controller 1460, which is arranged to facilitate communications with one or more other computing devices 1462 over a network communication link via one or more communication ports 1464. The one or more other computing devices 1462 include servers, mobile devices, and comparable devices.

The network communication link is an example of a communication media. The communication media are typically embodied by the computer-readable instructions, data structures, program modules, or other data in a modulated data signal, such as a carrier wave or other transport mechanism, and include any information delivery media. A "modulated data signal" is a signal that has one or more of its characteristics set or changed in such a manner as to encode information in the signal. By way of example, and not limitation, the communication media include: wired media (e.g., a wired network or a direct-wired connection) and wireless media (e.g., an acoustic wireless media, a radio frequency (RF) wireless media, a microwave wireless media, an infrared (IR) wireless media, etc.). The term "computer-readable media," as used herein, includes both storage media and communication media.

The system memory 1406, the removable storage devices 1436, and the non-removable storage devices 1438 are examples of the computer-readable storage media. The computer-readable storage media is a tangible device that can retain and store instructions (e.g., program code) for use by an instruction execution device (e.g., the computing device 1400). Any such, computer storage media is part of the computing device 1400.

In examples, the computer-readable instructions are provided to the processor 1404 of a general purpose computer, a special purpose computer, or another programmable data processing apparatus to produce a machine, such that the instructions, which execute via the processor 1404 of the computer or other programmable data processing apparatus, create means for implementing the functions/acts specified in the flowchart and/or block diagram block or blocks.

These computer-readable instructions are also stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions.

Another embodiment of the invention provides a method that performs the process steps on a subscription and/or fee basis. That is, a service provider can offer to create, maintain, and/or support, a computer infrastructure that performs the process steps associated with an improved tele-magnifier system for one or more customers. In return, the service provider can receive payment from the customer(s) under a subscription and/or fee agreement.

Likewise, claimed subject matter is, of course, not necessarily limited to one of the embodiments described. In the preceding description, various aspects of claimed subject matter have been described. For purposes of explanation, specific numbers, systems, or configurations may have been set forth to provide a thorough understanding of claimed subject matter. However, it should be apparent to one skilled in the art having the benefit of this disclosure that claimed subject matter may be practiced without those specific details.

In other instances, features that would be understood by one of ordinary skill may have been omitted or simplified so as not to obscure the claimed subject matter. While certain features have been illustrated, or described herein, many modifications, substitutions, changes, or equivalents may now occur to those skilled in the art. It is, therefore, to be understood that the appended claims are intended to cover all such modifications or changes as fall within the true spirit of claimed subject matter.

What is claimed is:

1. An improved binocular indirect ophthalmoscope (BIO), comprising:
   a BIO headset including:
   two distinct oculars including a left eye ocular and a right eye ocular;
   a left mirror positioned adjacent to and aligned with the left eye ocular;
   a right mirror positioned adjacent to and aligned with the right eye ocular;
   a central mirror block positioned between the left mirror and right mirror; and
   a viewing window positioned adjacent to and aligned with the central mirror block; and
   an integrated Galilean tele-microscope removably coupled to the BIO headset, adjacent to the viewing window included within the BIO headset, the integrated Galilean tele-microscope including at least:
   a first lens positioned adjacent to the viewing window and aligned with the central mirror block, and
   a second lens positioned adjacent to and separated from the first lens by a distance, the second lens aligned with the first lens, the central mirror block, and the viewing window included in the BIO headset,
   wherein the first lens is positioned between the viewing window of the BIO headset and the second lens, and
   wherein the integrated Galilean tele-microscope is further configured to magnify an image produced by a hand-held condensing lens, which is held in front of a patient's eye by an examiner approximately at 50 cm away from the examiner's eyes and operable to provide the examiner with an improved resolution view of a patient's fundus.

2. The improved BIO of claim 1, wherein:
   at least one of the first lens or the second lens of the integrated Galilean tele-microscope have design surfaces selected from a group consisting of: a spherical design, an aspheric design, and a combination thereof, and
   at least one of the first lens or the second lens of the integrated Galilean tele-microscope have a lens form selected from a group consisting of: a planoconcave lens form, a plano-convex lens form, a bi-concave lens form, a bi-convex lens form, a positive meniscus lens form, a negative meniscus lens form, and any combination thereof.

3. The improved BIO of claim 1, wherein the integrated Galilean tele-microscope further includes:
   a mechanism operative to vary a distance between the first lens and the second lens and configured to: focus an image of a fundus viewed using the improved BIO and set a working distance for the improved BIO.

4. The improved BIO of claim 1, further including a light source that selectively illuminates the patient's fundus.

5. An improved tele-magnifier system, comprising:
   a Galilean tele-microscope including a mount, the mount configured to detachably affix the Galilean tele-microscope to a binocular indirect ophthalmoscope (BIO) headset, adjacent to and aligned with a central mirror block and a viewing window included in the BIO headset, wherein the Galilean tele-microscope includes at least:
   a first lens positioned adjacent to the viewing window of the BIO headset, and
   a second lens positioned adjacent to and separated from the first lens by a distance, the second lens aligned with the first lens, the central mirror block, and the viewing window included in the BIO headset,
   wherein the first lens is positioned between the viewing window of the BIO headset and the second lens, and
   wherein the Galilean tele-microscope further includes a mechanism configured to vary the distance separating the first lens and the second lens to focus an image of a fundus viewed using the Galilean tele-microscope and set a working distance of approximately 50 cm for the improved tele-magnifier system.

6. The improved tele-magnifier system of claim 5, wherein:
   at least one of the first lens or the second lens of the Galilean tele-microscope have design surfaces selected from a group consisting of: a spherical design, an aspheric design, and a combination thereof, and
   at least one of the first lens or the second lens of the Galilean tele-microscope have a lens form selected from a group consisting of: a plano-concave lens form, a plano-convex lens form, a bi-concave lens form, a bi-convex lens form, a positive meniscus lens form, a negative meniscus lens form, and any combination thereof.

7. The improved tele-magnifier system of claim 5, wherein the Galilean tele-microscope includes a self-contained housing affixed to a front of the BIO by the mount.

8. The improved tele-magnifier system of claim 5, wherein the mount is customizable based on the self-contained housing and an associated BIO make and model.

9. The improved tele-magnifier system of claim 5, wherein the mount is selected from a group consisting of: a flip away mount, a flip up mount, a flip side mount, a flip down mount, a clip on mount, a press on mount, a magnetic mount, and any combination thereof.

10. The improved tele-magnifier system of claim 5, wherein:
the Galilean tele-microscope is configured to attach to the BIO via one or more detachable mounting mechanisms, and
the one or more detachable mounting mechanisms are selected from a group consisting of: a clip-on detachable mounting mechanism, a grip-on detachable mounting mechanism, a screw-on detachable mounting mechanism, a magnetic detachable mounting mechanism, and any combination thereof.

11. The improved tele-magnifier system of claim 5, further including a light source that selectively illuminates the fundus.

12. An optical attachment capable of affixation to a first position on a binocular indirect ophthalmoscope (BIO) headset placed in front of a viewing window of the BIO headset, the optical attachment comprising:
a first lens positioned adjacent to the viewing window of the BIO headset;
a second lens positioned adjacent to and separated from the first lens by a distance, the second lens aligned with the first lens, and
the viewing window included in the BIO headset,
wherein the first lens is positioned between the viewing window of the BIO headset and the second lens; and
one or more mechanisms configured to vary the distance between the first lens and the second lens to focus the optical attachment on an image of a fundus at a working distance of approximately 50 cm therefrom.

13. The optical attachment of claim 12, wherein:
at least one of the first lens or the second lens have design surfaces selected from a group consisting of: a spherical design, an aspheric design, and any combination thereof, and
at least one of the first lens or the second lens have a lens form selected from a group consisting of: a plano-concave lens form, a plano-convex lens form, a bi-concave lens form, a bi-convex lens form, a positive meniscus lens form, a negative meniscus lens form, and any combination thereof.

14. The optical attachment of claim 12, wherein the one or more mechanisms to adjust the distance separating the first lens and the second lens are selected from a group consisting of: a rotation mechanism, a slide mechanism, and any combination thereof.

15. The optical attachment of claim 12, wherein:
the optical attachment is located within a self-contained housing, and
the one or more mechanisms are configured to at least one of rotate or slide the self-contained housing to focus the optical attachment.

16. The optical attachment of claim 12, wherein:
an adjustment of: at least one of a magnification of the optical attachment or the distance at which the optical attachment focuses is based on one or more parameters, and
the one or more parameters are selected from a group consisting of: a power of the first lens, a power of the second lens, a lens form of the first lens, a lens form of the second lens, a design surface of the first lens, a design surface of the second lens, the distance between the first lens or the second lens, and any combination thereof.

17. The optical attachment of claim 16, wherein:
the lens form of the first lens and the lens form of the second lens are selected from a group comprising: a plano-concave lens form, a plano-convex lens form, a bi-concave lens form, a bi-convex lens form, a positive meniscus lens form, a negative meniscus lens form, and any combination thereof, and
the design surface of the first lens and the design surface of the second lens are selected from a group comprising: a spherical design surface, an aspheric design surface, and any combination thereof.

18. The optical attachment of claim 12, wherein the optical attachment is configured to be removed or to move to a second position by one or more movements selected from a group consisting of: a removable movement, a detachable movement, a flipping movement, a sliding movement, a rotating and moving up movement, a rotating and moving down movement, a rotating away and to the side movement, and any combination thereof, wherein, at the second position, the optical attachment un-obstructs the viewing window of the BIO.

19. The optical attachment of claim 18, wherein, the self-contained housing of the optical attachment may be detached from its mounting mechanism and re-attached to another mounting mechanism of a different design to accommodate mounting to other existing BIO instruments.

20. The optical attachment of claim 12, further including a light source that selectively illuminates the fundus.

* * * * *